United States Patent [19]

Gruber

[11] Patent Number: 5,132,291
[45] Date of Patent: Jul. 21, 1992

[54] ANTIVIRALS AND METHODS FOR INCREASING THE ANTIVIRAL ACTIVITY OF AZT

[75] Inventor: Harry E. Gruber, San Diego, Calif.

[73] Assignee: Gensia Pharmaceuticals, Inc., San Diego, Calif.

[21] Appl. No.: 301,454

[22] Filed: Jan. 24, 1989

[51] Int. Cl.$^5$ .............................................. A61K 31/70
[52] U.S. Cl. ...................................... 514/43; 514/49; 514/50; 514/934
[58] Field of Search .................................. 514/45-50, 514/43, 934

[56] References Cited

U.S. PATENT DOCUMENTS

| | | | |
|---|---|---|---|
| 4,321,366 | 3/1982 | Bobek et al. | 536/55 |
| 4,575,498 | 3/1986 | Holmes et al. | 514/43 |
| 4,724,232 | 2/1988 | Rideout et al. | 514/50 |
| 4,847,244 | 7/1989 | Rideout et al. | 514/50 |
| 4,874,751 | 10/1989 | Beacham, III et al. | 514/50 |
| 4,880,782 | 11/1989 | Eckstein et al | 514/45 |

OTHER PUBLICATIONS

"Antiviral Therapy in AIDS: Clinical Pharmacological Properties and Therapeutic Experience to Date"; Drugs, vol. 34, 1987 pp. 372–390 (E. G. Sandstrom).
Aids Research and Human Retroviruses, vol. 4, No. 6, issued 1988, "Nucleotide Dimers Suppress HIV Expression In Vitro" See pp. 449–455 (Mariano Busso, et al.).
Kalman et al., Nucleosides & Nucleotides, 8:899–902, 1989.
Hao et al., Mol. Pharm. 34:431–435, 1988.

Primary Examiner—John W. Rollins
Attorney, Agent, or Firm—Lyon & Lyon

[57] ABSTRACT

Antiviral purine nucleosides, purine nucleoside analogs and prodrugs of both are provided. Also provided are methods of enhancing the antiviral activity of AZT by administering AZT in combination with such purine compounds.

50 Claims, 9 Drawing Sheets

FIG. 4a. HIV CEM SYNCITIAL ASSAY

★ $p < 0.05$
★★ $p < 0.01$

★ p<0.05
★★ p<0.01

EFFECT OF TIME AND AICA rib. CONCENTRATION ON SAHH ACTIVITY

Ki = 90
Kmax = 0.02/min

ANTIVIRALS AND METHODS FOR INCREASING THE ANTIVIRAL ACTIVITY OF AZT

BACKGROUND OF THE INVENTION

The present invention is directed to antiviral purine nucleosides, purine nucleoside analogs, and prodrugs of both. It is also directed to processes for increasing the antiviral activity of the compound 3'azido-3'deoxythymidine ("AZT") by administering AZT in combination with such purine compounds.

AZT has shown promise as an antiviral agent, useful in the treatment of certain viral infections which are believed to be caused by retroviruses. In particular, AZT has shown promise against the human immunodeficiency virus.

AZT is currently in use for the treatment of AIDS in patients with AIDS related complex and for use in AIDS patients who have had recent episodes of pneumocytis carinii-related pneumonia. It appears to be effective in decreasing levels of human immunodeficiency virus ("HIV") antigen in human blood peripheral monocytes. Chaisson et al., *N. Engl. J. Med.*, Vol. 315, p. 1610–1611 (1986).

AZT is a thymidine analog in which the 3'-hydroxy group is replaced with an azido group. On entering the cell, AZT is phosphorylated to AZT monophosphate by the same cellular kinase which phosphorylates thymidine. AZT monophostate is then phosphorylated to the diphosphate and triphosphate forms by other cellular kinases. AZT triphosphate is said to interfere with retroviral RNA dependent DNA polymerase (or "reverse transcriptase"), thus inhibiting viral replication. In vitro tests have also been said to support a mechanism whereby AZT triphosphate is incorporated by virus reverse transcriptase into DNA copies of HIV after the virus enters the cell and begins to replicate. The growing DNA chairs which incorporate AZT triphosphate are thereby permaturely terminated because AZT cannot receive an additional nucleotide at the 3' position. AZT has a somewhat greater affinity for viral reverse transcriptase than for human DNA polymerases. Thus, HIV replication can be slowed without blocking cellular replication.

The phosphorylation of AZT to AZT monophosphate by thymidine kinase has been suggested as the rate limiting step in this process. Richman and Carson, *Journal of Experimental Medicine*, Vol. 166, p. 1141–1149 (October, 1987). Richman and Carson stated that AZT could not be phosphorylated to the triphosphate form in the peripheral blood macrophages of normal humans in high enough concentrations to inhibit the AIDS virus reverse transcriptase. They suggested that the low level of incorporation of AZT was related to a four-fold lower level of the enzyme thymidine kinase as compared to the lymphoblast line CEM. It was reported that this lower activity of thymidine kinase was associated with a nine-fold lower accumulation of AZT nucleotides, and that the nine-fold lower level of AZT nucleotides was associated with a 100 to 1000 fold reduction in antiviral activity in macrophages as compared to CEM cells.

It is suggested here that at least two important parameters affect how much AZT triphosphate is incorporated into newly formed viral nucleic acids and/or how effectively reverse transcriptase is inhibited: (1) the amount of AZT triphosphate present and (2) the amount of thymidine triphosphate "TTP") present. It is believed that AZT triphosphate competes with TTP for incorporation into newly synthesized nucleic acids. Thus, a portion of the reduction in effectiveness of AZT reported by Richman and Carson may have been related to factors other than phosphorylation; for example, macrophages may have inherently higher TTP pools than CEM cells. TTP pools were, however, not measured. The importance of the amount of TTP present as a parameter for AZT incorporation is supported by the effect of the drug ribavirin on HIV replication in the presence of AZT. Boght et al., *Science*, Vol. 235, p. 1376–1379 (March, 1987), reported that ribavirin reduced the effectiveness of AZT against the AIDS virus in both peripheral blood lymphocytes and H9 cells and that ribavirin decreased phosphorylation of AZT to the mono-, di-, and triphosphate forms by approximately a factor of ten in both AIDS infected and uninfected cells. The authors proposed that ribavirin could act by diminishing AZT triphosphate formation through an increase in the TTP pool which results in a feedback inhibition of the enzyme thymidine kinase, thus reducing the phosphorylation of AZT to AZT triphosphate by that enzyme, or by reducing the interaction of AZT triphosphate with the HIV reverse transcriptase enzyme.

The use of AZT does have certain drawbacks. It is unknown, for example, whether AZT can be tolerated over a prolonged time. Current clinical experience is still limited to a certain extent and the long-term effects of chronic AZT treatment remain to be evaluated. It is known, on the other hand, that AZT has numerous side effects, including bone marrow toxicity. Thus, the most common side effect is macrocytic anemia, which may be severe enough to require blood transfusions, and which has been reported to eventuate in up to 45% of patients having a CD4 (T4) lymphocyte count of $\leq 200/mm^3$. Granulocytopenia has been reported to occur in up to 55% of patients having a CD4 count of $\leq 200/mm^3$ and in up to 40% of patients with CD4 count of $>200/mm^3$ (19% and 13% of these patients, respectively, showed granulocytopenia with placebo); Physician's Desk Reference, page 820 (42d Edition 1988). It is possible that patients with folate or vitamin B12 deficiencies may be more sensitive to the bone marrow depression caused by AZT. In many cases, patients can tolerate a reduced dose of AZT with resultant improvement in white blood cell count and anemia. Severe headache, nausea, insomnia and myalgia are also reported at a significantly greater rate in AZT recipients. Id.

AZT has also been shown to have anti-bacterial activity. There have been reports of an enhanced effect from treatment of bacteria with both AZT and the anti-folate antibiotics, namely the sulfonamides. See Elwell et al., *Antimicrobial Agents and Chemotherapy*, Vol. 31, p. 274 (1987). The authors did not speculate on the mechanism of the observed increased sensitivity to AZT in the presence of sulfonamides; however, they did report their clinical observations that treatment of patients having pneumocystis carini pulmonary infection with both AZT and sulfonamides appeared useful.

The enzyme S-adenosylhomocysteine ("SAH") hydrolase catalyzes the reversible hydrolosis of S-adeonylhomocysteine to adenosine and L-homocysteine. When the concentration of these substrates is higher than in the micromolar range, the reaction favors synthesis. Ueland, *Pharmalogical Reviews*, Vol. 34, p.

223-253 (1982). There are a number of acyclic and carbocyclic analogs of adenosine which are reported to owe their antiviral activity to inhibition of SAH hydrolase. De Clercq, *Biochemical Pharmacology*, Vol. 36, p. 2567-2575 (1987). No SAH hydrolase inhibitors have been reported to have anti-human retroviral or anti-HIV activity.

Pharmacologic properties of AICA riboside (5-amino-1-β-D-ribofuranosyl-imidazole-4-carboxamide), including metabolism and metabolic effects, were described by Thomas et al., *Journal of Cellular Physiology*, Vol. 103, p. 335-344 (1981). AICA riboside was discovered in the 1950's in the culture media of bacteria grown in the presence of sulfonamide antibiotics. The antifolate properties of the sulfonamides cause a block in purine metabolism that causes a build up of AICA riboside monophosphate in the cells which is then catabolized and excreted as AICA riboside. Following studies using Chinese hamster lung fibroblasts Thomas et al. wrote that AICA riboside, at a concentration of 200 $\mu$M, arrested cell growth associated with pyrimidine starvation which was reversed by addition of the pyrimidine uridine. The article also refers to a vast literature on the toxic effects of purine nucleosides such as adenosine and deoxyadenosine on cell growth. Other compounds, such as EHNA and deoxycoformycin, which inhibit adenosine deaminase and cause a build up of adenosine and deoxyadensine, are also cytotoxic through pyrimidine starvation. These other molecules have additional cytotoxic effects in addition to simple pyrimidine starvation. Studies have been done on adenosine and deoxyadenosine as cytotoxic immunosuppressive compounds. Gruber et al., *Annals of the New York Academy of Science*, Vol. 51, p. 315-318 (1985).

Work on AICA riboside by Thomas et al., supra, led to their conclusion of an expansion of the ATP and GTP pools combined with a depression of the phosphoribosyl-pyrophosphate (PRPP) pool at 200 $\mu$M AICA riboside. The purine pool (ATP and GTP) was said to have been expanded by about 40% at 50 $\mu$M and 200 $\mu$M AICA riboside. At 50 $\mu$M and 200 $\mu$M AICA riboside, the PRPP availability, as measured by adenine incorporation, dropped by 18% and 82% respectively. It was believed that the continued effect of an increase in the purine pools and a decrease in PRPP availability resulted in an inhibition of the enzyme orotate phosphoribosyl transferase-orotate decarboxylase (OPRT-ODC). This enzyme converts orotate into uridine monophosphate. Cells grown at concentrations of 50 $\mu$M and 200 $\mu$M AICA riboside exhibited a reduced growth rate which was reversible by the addition of uridine to the growth media and which showed an accompanying increase in orotate pools in the growth media surrounding those cells. Thomas et al. concluded that AICA riboside caused pyrimidine starvation by its effects on the ATP, GTP and PRPP pools. The inhibitory effects reported appear to be the result solely of pyrimidine starvation, whereas other compounds which caused pyrimidine starvation had numerous other cytotoxic effects.

Thomas et al. also reported that UTP and CTP pools decreased by a factor of approximately ten. TTP pools were not measured It was reported that at a much higher dose, 700 $\mu$M AICA riboside, the ATP and GTP pools were no longer elevated but there was still a reduction in the PRPP pools. At that AICA riboside concentration and with that combination of observed effects there was no cytotoxicty, no oratate excretion, but still a depletion of UTP and CTP. Because there was still normal growth, the lack of oratate may have indicated a compensated pyrimidine depletion.

While AZT is the first antiviral agent to be marketed with an indication for the treatment of AIDS, it is acknowledged to be very expensive and toxic, it requires frequent dosing, and it is available only in limited supply. Thus, it will be understood that more readily available antiviral agents having less toxicity, or agents which will lessen the side effects of AZT, or both, are desired and would be of great utility. The present invention provides such agents.

SUMMARY OF THE INVENTION

The present invention is directed to the use of certain purine nucleosides and nucleotides or analogs or prodrugs of either as antivirals and, further, to a method of increasing the antiviral, antibacterial and antiparasitic activity of AZT which comprises administering AZT in combination with a therapeutically effective amount of such a purine compound. Preferred antiretroviral purine compounds are those which function to decrease TTP levels or which function to inhibit the enzyme S-adenosyl-homocysteine hydrolase or both. The antiviral and antiretroviral purine nucleosides include AICA, AICA riboside, and carbocyclic AICA riboside, AICA riboside being preferred. Preferred antiviral and antiretroviral purine nucleoside prodrugs include 5-amino-3'-(2-methyl-1-propoxycarbonyl)-1-β-D-ribofuranosyl-imidazole-4-carboxamide, 5-amino-3'-(1-propoxycarbonyl)-1-β-D-ribofuyranosyl-imidazole-4-carboxamide, and 2',3'-cyclocarbonate AICA riboside. The former prodrug also appears to have some analog activity.

Among other factors, the present invention relates to the discovery that the purine nucleoside AICA riboside, AICA riboside prodrugs, and certain AICA riboside analogs have antiviral activity and that the combination of AZT with these compounds increases the antiviral activity of AZT. Observed increases in the antiviral effect of AZT include those on the order of a factor of approximately ten or greater. Accordingly, by using AZT in conjunction with such purine nucleosides or analogs, or prodrugs of them, the concentration of AZT required may be decreased, thereby decreasing AZT-related side-effects and toxicity, the dosing frequency, and also decreasing the expense of AZT treatment.

In a related aspect, the present invention is directed to a method of decreasing or preventing replication of a virus, particularly a retrovirus, which comprises administering a therapeutically effective amount of AZT in conjunction with a therapeutically effective amount of a purine nucleoside or analog, or prodrug of either, which increases the incorporation of AZT triphosphate into DNA by reverse transcriptase.

In another aspect, the present invention is directed to a method of decreasing or preventing replication of a retrovirus, especially a human retrovirus, which comprises administering a therapeutically effective amount of an SAH hydrolase inhibitor. It has been determined that AICA and AICA riboside are potent inhibitors of SAH hydrolase, even at a concentration as low as 10 $\mu$M. The above noted purine nucleoside analogs and prodrugs also function to inhibit SAH hydrolase. These purine nucleosides may be administered without AZT to decrease or prevent viral replication, and may be used alone for the treatment of patients with AIDS or HIV infections.

Certain anticancer drugs appear to compete with TTP for incorporation into nucleic acids. Their activities are believed to be limited by their rate of phosphorylation. Accordingly, in a further aspect, the present invention is directed to increasing the activities of those drugs, e.g., 5-fluorouracil and 2'-deoxy-5-fluorouridine, by administering them in conjunction with a purine nucleoside or analog such as AICA riboside which decreases TTP levels.

The dose of the compounds of the invention for the uses described above will normally be in the range of about 1 to about 1000 mg/kg/day, preferably from about 10 to about 300 mg/kg/day, especially about 10 to about 100 mg/kg/day.

BRIEF DESCRIPTION OF THE DRAWINGS

FIG. 4(a). Reduction in the virus titer as a percent of control averaged from three experiments on HIV infected CEM T cells, each done in triplicate, using [(a)] AICA riboside [and (b) AZT]. The p values compare treated with untreated cells.

DEFINITIONS

Figure 1A:
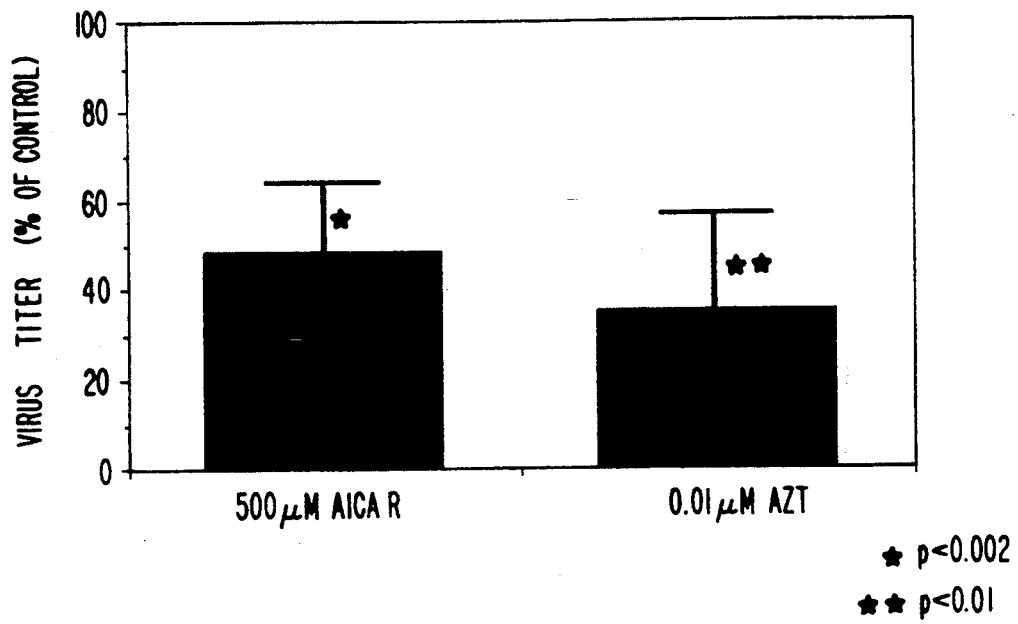
FIG. 1(a). The antiviral effects of AICA riboside and AZT using a murine vector ("BAG") packaged by a murine virus ("MA") in the human macrophage cell line U937, carried to a rat fibroblast line and selected in neomycin. The p values compare treated with untreated cells.

As used herein, the following terms have the following meanings, unless expressly stated to the contrary:

The term "alkyl" refers to saturated aliphatic groups, including straight, branched and carbocyclic groups.

The term "alkenyl" refers to unsaturated alkyl groups having at least one double bond [e.g., $CH_3CH=CH(CH_2)_2-$] and includes both straight and branched-chain alkenyl groups.

The term "alkynyl" refers to unsaturated groups having at least one triple bond [e.g., $CH_3C\equiv C(CH_2)_2-$] and includes both straight chain and branched-chair groups.

The term "aryl" refers to aromatic hydrocarbyl and heteroaromatic groups which have at least one aromatic ring.

The term "alkylene" refers to straight and branched-chain alkylene groups which are biradicals, and includes, for example, groups such as ethylene, propylene, 2-methylpropylene

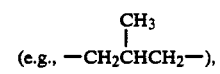

3-methylpentylene

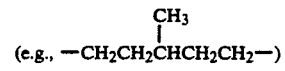

and the like.

The term "hydrocarbyl" denotes an organic radical composed of carbon and hydrogen which may be aliphatic (including alkyl, alkenyl, and alkynyl groups and groups which have a mixture of saturated and unsaturated bonds), alicyclic (carbocyclic), aryl (aromatic) or combinations thereof; and may refer to straight-chained, branched-chain or cyclic structures or to radicals having a combination thereof; as well as radicals substituted with halogen atom(s) or heteroatoms such as nitrogen, oxygen and sulfur and their functional groups (such as amino, alkoxy, aryloxy, lactone groups and the like) which are commonly found in organic compounds and radicals.

The term "hydrocarbyloxycarbonyl" refers to the group

wherein R' is a hydrocarbyl group.

The term "hydrocarbylcarbonyl" refers to the group

wherein R' is a hydrocarbyl group.

The term "ester" refers to a group having a

linkage, and includes both acyl ester groups and carbonate ester groups.

The term "halo" or "halogen" refers to fluorine, chlorine, bromine and iodine.

The term "carbonate ester" refers to the group

wherein R' is hydrocarbyl, and to compounds having at least one such group.

The term "acyl ester" refers to the group

wherein R' is hydrocarbyl, and to compounds having at least one such group.

The term "mixed ester" refers to compounds having at least one carbonate ester group and at least one acyl ester group.

DETAILED DESCRIPTION OF THE INVENTION

The present invention is directed to the use of purine nucleoside antivirals and to methods of increasing the antiviral, antibacterial and antiparasitic activity of AZT, in particular to methods of increasing the efficacy of AZT against retroviruses such as the AIDS (HIV) virus. The invention provides for the use of AICA riboside, AICA riboside prodrugs and certain AICA riboside analogs and analog prodrugs as antiviral, particularly antiretroviral, agents. The invention also provides for methods of preventing or reducing retroviral activity by the inhibition of SAH hydrolase and by decreasing thymidine triphosphate pools.

The effects of the use of these purine nucleoside compounds, including AICA riboside, as antivirals and for increasing the antiviral activity of AZT have been demonstrated in vitro. These purine nucleoside compounds will be used to enhance the activity of AZT in treating viral, bacterial and parasitic infections in patients. To deliver these molecules to patients, it is anticipated that they will most often be administered orally. These compounds can also be administered intravenously, by direct intramuscular injection, subcutaneously, topically to skin or mucous membranes, rectally or by inhalation. Compositions acceptable for pharmaceutical use are well known. Useful prodrugs are those which, when introduced into the body, metabolize to their active AICA riboside form. Other prodrugs are those which metabolize to carbocyclic AICA riboside ("(±)-5-Amino-1-[β-2'α,3'α-dihydroxy-4'β-(hydroxymethyl)-cyclopentyl]imidazole-4-carboxamide").

Since the purine nucleoside AICA riboside can be metabolized to uric acid, this compound may be used with allopurinol or other drugs that prevent uric acid synthesis, or with a uricosuric agent such as probenecid. Certain agents, such as methotrexate, whose metabolites inhibit AICA ribotide transformylase, may also be used in conjunction with the compounds of the invention. They can cause an elevation of endogenously synthesized AICA ribotide. Furthermore, carbocyclic AICA riboside, which does not break down to uric acid, may be used to combat viral infectivity or to enhance the activity of AZT.

By a number of experiments, AICA riboside has been demonstrated to be an effective antiviral agent. AICA riboside is believed to cause a reduction in TTP pools and, thus, an elevation in thymidine kinase activity. This in turn enhances the ability of AZT triphosphate to compete with TTP for the reverse transcriptase enzyme and for incorporation into viral nucleic acids. AICA and AICA riboside have also been discovered to be very potent inhibitors of S-adenosyl-homocysteine "SAH") hydrolase, an enzyme which converts SAH to adenosine and homocysteine. Inhibition of this enzyme causes a build-up of SAH, which in turn inhibits the enzymatic conversion of S-adenosyl methionine "SAM") to SAH. This latter inhibition can cause the destablization of viral mRNA which is normally stabilized by 5' methylation generated through the conversion of SAM to SAH.

Administration of AZT and AICA riboside, for example, in conjunction with one another, either together in one formulation or separately, should have at least additive effects. In addition, any one of the de novo purine nucleoside synthesis intermediates (after the first committed step for purine synthesis) or their nucleosides or bases can be assumed to be rapidly converted to AICA ribotide and will be useful. An example is SAICA (succinylaminoimidazolecarboxamide) ribotide or its nucleoside or base. Other examples include aminoimidazole carboxylic acid riboside.

As set forth in Examples Three and Four below, the results of which are in part shown in FIG. 6, the administration of AICA riboside at only 50 μM in conjunction with AZT has been found to dramatically increase the anti-viral activity for a given dose of AZT. AICA, AICA riboside, and the derivative compounds described and claimed herein may be used to enhance the antiviral activity of AZT against viruses and in particular against retroviruses and human retroviruses, including HIV.

It is the triphosphate form of AZT which is thought to be antiviral. AZT enters cells and is phosphorylated to the triphosphate. In retroviruses, in addition to inhibiting reverse transcriptase, AZT triphosphate is thought to be incorporated into DNA by reverse transcriptase and act as a chain terminator. While not being bound by the following proposed modes of action, it is believed that these compounds assist AZT triphosphate in competing with TTP for incorporation in the viral DNA by the viral reverse transcriptase and, further, by destabilizing synthesized viral nucleic acids through the prevention or lessening of methylation following inhibition of SAH hydrolase. Hypomethylation of other cellular constituents such as membrane phospholipids and proteins may also contribute to this anti-viral activity.

Treatment with such purine nucleosides as AICA riboside, in addition to SAH hydrolase inhibition, should cause a reduction in TTP pools and, therefore, an elevation in thymidine kinase activity and an increase in the ability of AZT triphosphate to compete with TTP for incorporation into newly formed nucleic acids by retroviral reverse transcriptase. With regard to the latter mode of action, it is believed that purine nucleosides or analogs such as AICA riboside cause a pyrimidine starvation effect which decreases the TTP pool (as well as the CTP and UTP pools), and that the decrease in the TTP pool is coupled with an increase in the activity of thymidine kinase, which has been postulated to be the rate-limiting step in phosphorylating AZT to AZT triphosphate. Treatment with purine nucleosides or analogs such as AICA riboside is believed to result in decreased levels of TTP and increased levels of AZT triphosphate, with the result that more AZT triphosphate is incorporated into the viral DNA by the retroviral reverse transcriptase or inhibiting it and, thus, a more efficient antiviral activity per AZT treatment.

The proposed action of purine nucleosides such as AICA riboside as antivirals, and as agents which enhance the sensitivity of retroviruses to AZT, was tested using several retroviral assays. The assays were conducted using cells in culture. In Example One, the effects of AICA riboside and AZT on cell growth were evaluated. As shown in FIG. 8, it was demonstrated that the combination of AZT and AICA riboside did not cause a decrease in B-cell growth, and only at 500 $\mu$M AICA riboside was T-cell growth selectively altered. FIG. 9 shows similar results with AICA-riboside added alone to two T-cell lines (CEM and SupT-1) and a B-cell line (WI-L2).

As described in Example Two, several retroviral assay systems were utilized to test the antiviral activity of various purine nucleoside compounds. One assay system employed a replication-defective murine leukemia virus construct "N2" containing a selectable marker (the neomycin resistance gene). The N2 virus construct is present in the producer or "helper" cell line also called N2 which contains a second retroviral construct that encodes for the production of the retrovirus proteins necessary for packaging and which can, therefore, psuedotype the N2 vector into an infective amphotrophic murine retrovirus. This infective retrovirus, which now contains a neomycin resistance gene, is obtained from the producer line and used to infect cells, in this case 208F rat fibroblast cells, having no neomycin resistance.

Figure 1B:
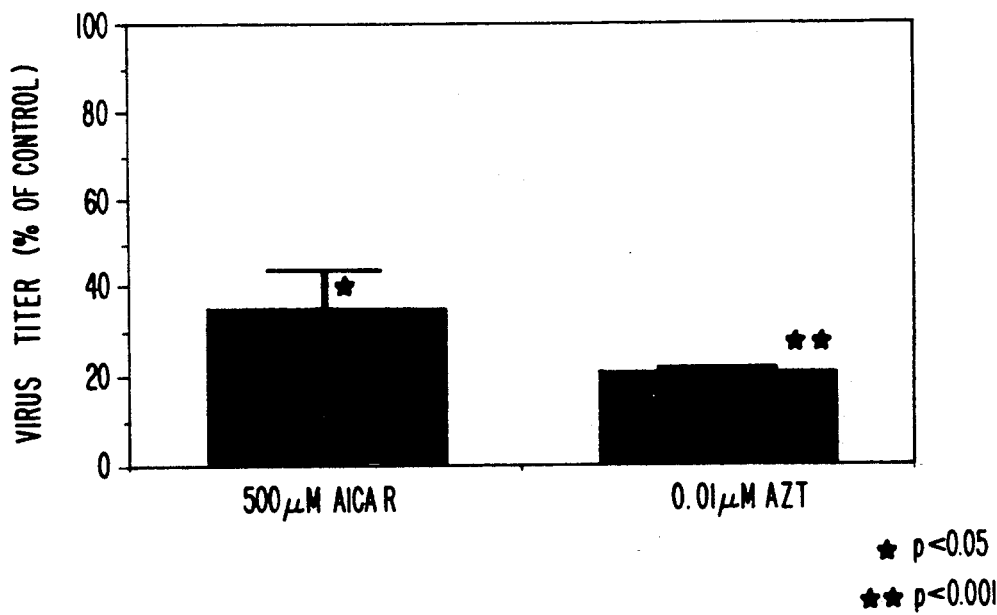
FIG. 1(b). The antiviral effects of AICA riboside and AZT using a neomycin resistance gene-containing vector "N2") packaged by a murine helper cell and infecting rat fibroblasts. The p values compare treated with untreated cells.

The 208F cells were treated, or not treated, with a selected antiviral drug. Neomycin was then introduced to the cultured cells. Only those cells which contain the neomycin resistance gene carried by a retrovirus not killed by the antiviral drug will grow and, therefore, the smaller the number of colonies the more effective is the antiviral drug. In other words, in this assay, each colony represented one virus particle which had entered a cell but was not killed by the antiviral drug, thus allowing the cell to grow into a colony in the presence of neomycin. Good correlation between anti-murine retroviral activity and anti-human retroviral activity has been observed. The 208F rat fibroblast line is that described by Miller et al., PNAS, Vol. 80, p. 4709–4713 (1983). Triplicate petri dishes were used for each experimental point. FIGS. 1b and 1c show the results of these assays. In the N2 colony assay, 0.01 $\mu$M AZT was shown to have somewhat better antiviral activity than 500 $\mu$M AICA riboside.

A second, similar assay system was utilized in which a human macrophage line (U937) carrying the BAG retroviral vector construct (having neomycin resistance and beta-galactosidase marker genes), Cepko, PNAS, Vol. 84, p. 156–160 (1987), was infected with MA (amphotrophic MLV [murine leukemia virus]). MA was used to pseudotype the replication-defective BAG vector, which was then titered on 208F cells. According to this assay, the results of which are shown in FIG. 1c, 0.01 $\mu$M AZT and 500 $\mu$M AICA riboside were both effective against murine retroviruses. The data found in FIG. 1 are similar to those of further experiments showing the effect of AZT and AICA riboside on human CEM cell lines infected with the human retrovirus HIV.

Figure 2A:
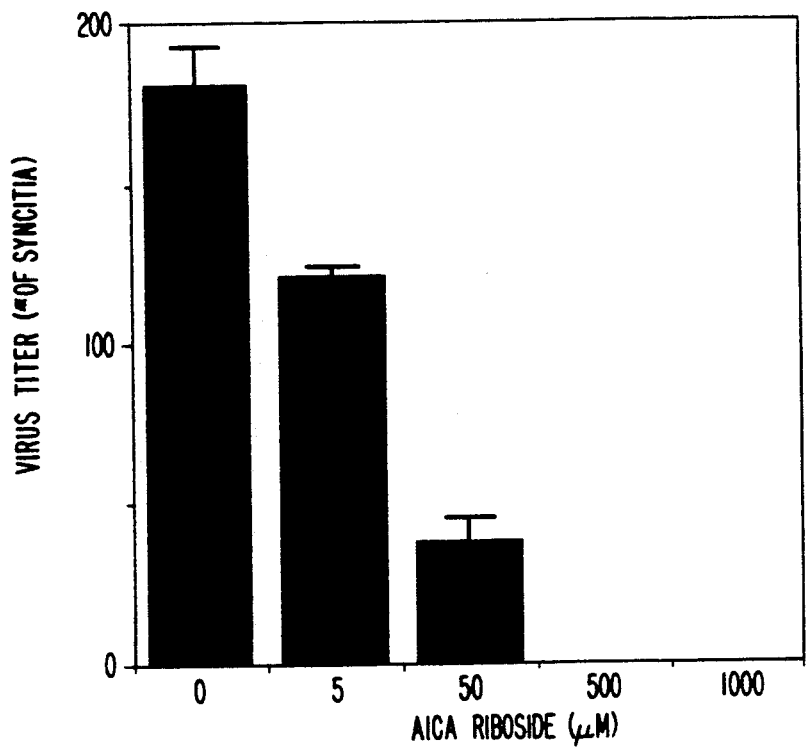
FIG. 2(a). Reduction in the virus titer (number of syncitia) following 24 hour preincubation of the CEM human T cell line with [(a)] AICA riboside [and AZT] prior to infection with HIV.
Figure 2B:
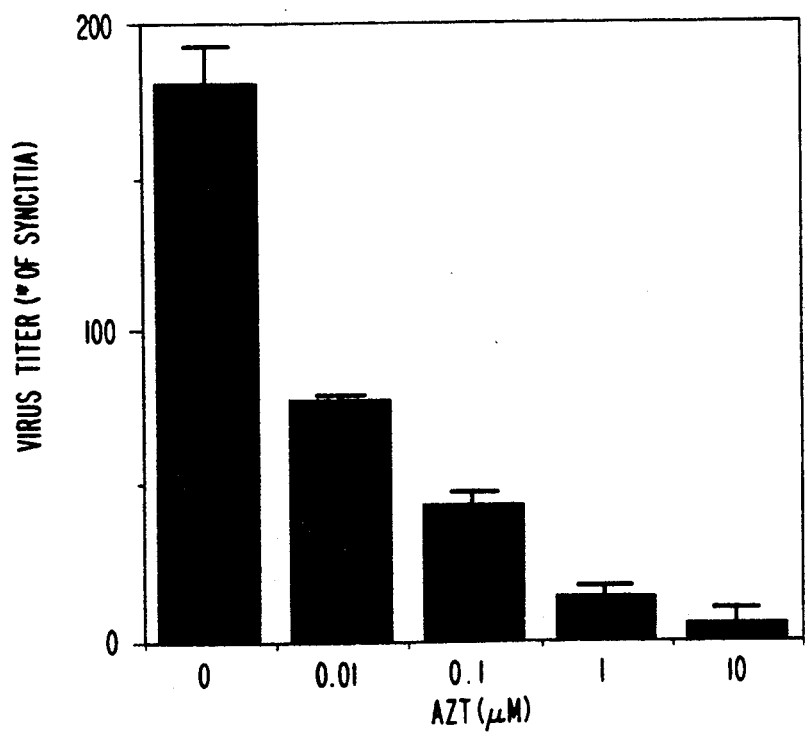
FIG. 2(b). Reduction in the virus titer (number of syncitia) following 24 hour preincubation of the CEM human T cell line with AZT prior to infection with HIV.
Figure 3:
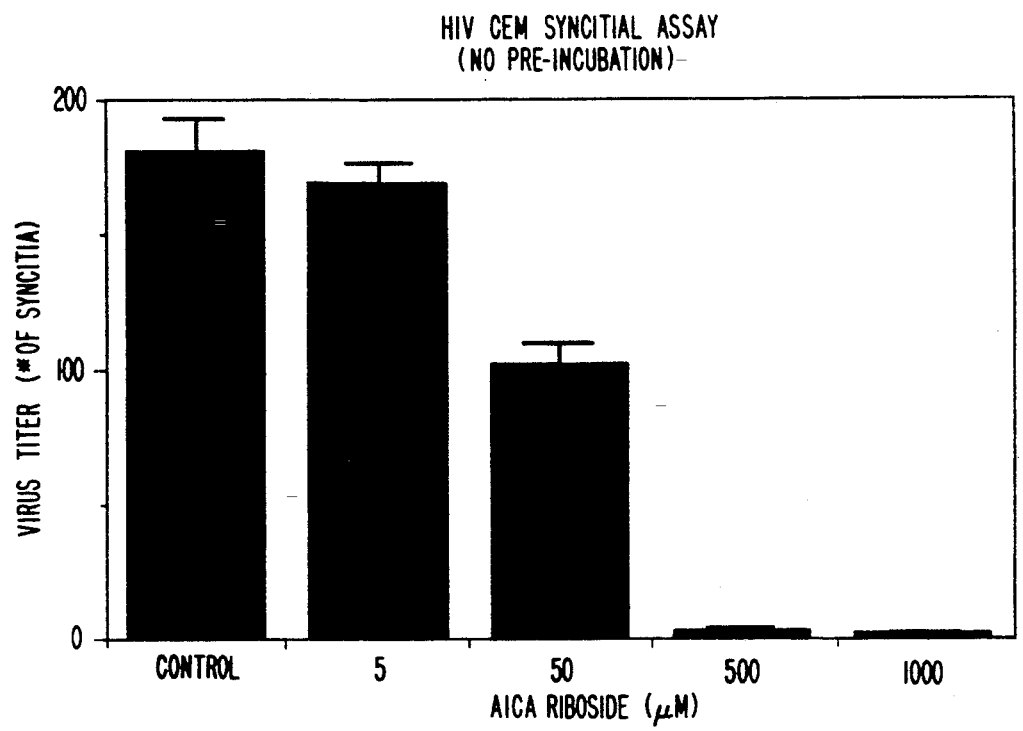
FIG. 3. Reduction in the virus titer (number of syncitia) by addition of AICA riboside to the CEM human T cell line at the time of infection with HIV.

The results of Example Three, wherein AICA riboside or AZT were preincubated prior to HIV infection in the CEM syncitial assay, are shown in FIG. 2. AICA riboside showed antiviral effect at 5 $\mu$M and 50 $\mu$M dosages, similiar to the antiviral effects of 0.01 $\mu$M and 0.1 $\mu$M AZT dosages. The results of similar experiments in which the cells were not preincubated with AICA riboside prior to infection are set forth in FIG. 3. These results indicate that AICA riboside was more effective as an antiviral with preincubation.

Figure 4B:
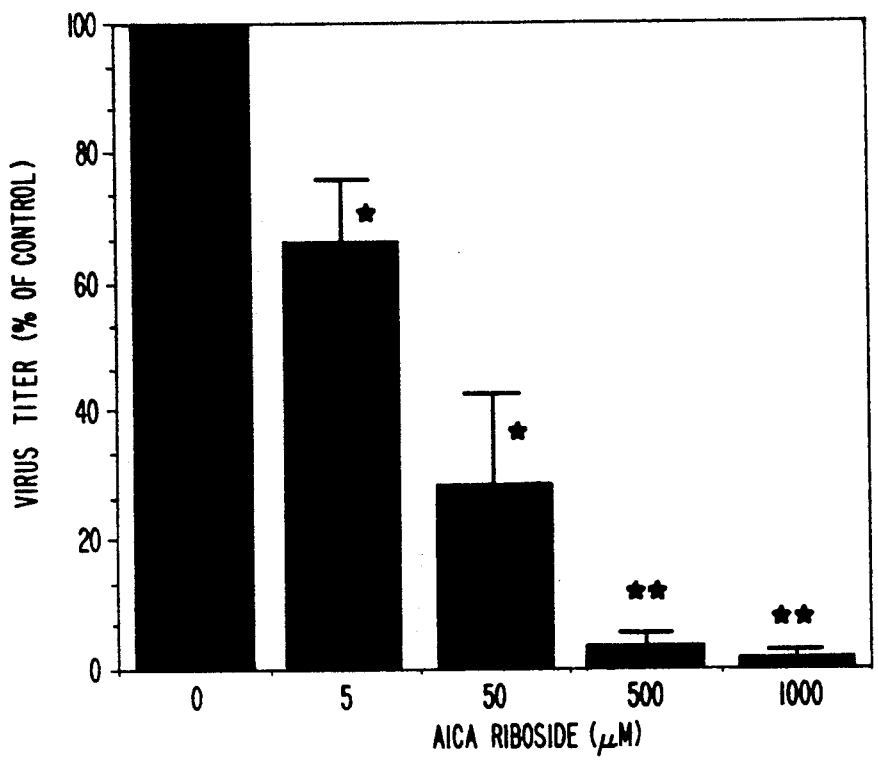
FIG. 4(b). Reduction in the virus titer as a percent of control averaged from three experiments on HIV infected CEM T cells, each done in triplicate, using AZT. The p values compare treated with untreated cells.
Figure 4B:
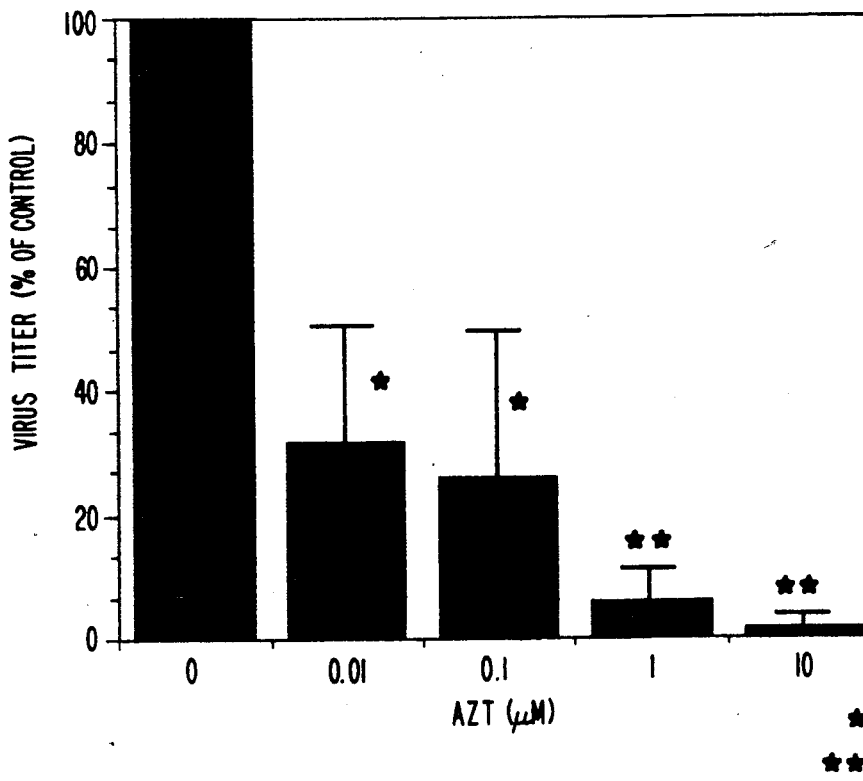
Figure 5A:
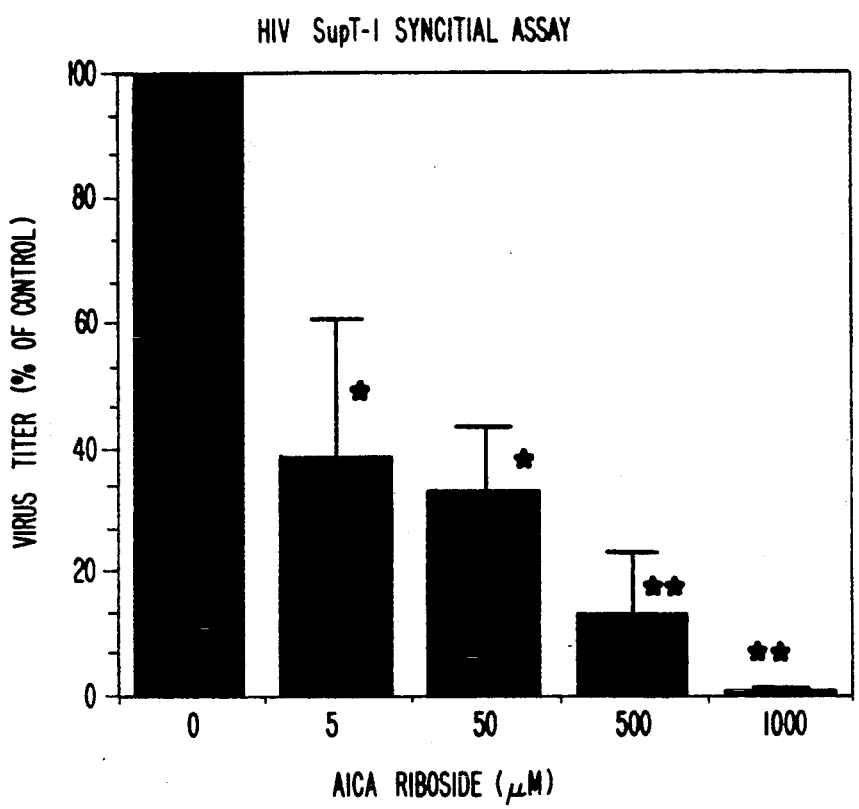
FIG. 5(a). Reduction in the virus titer as a percent of control following 24 hour preincubation of the HIV infected T cell line SupT-1 with [(a)] AICA riboside [and (b) AZT]. The p values compare treated with untreated cells.
Figure 5B:
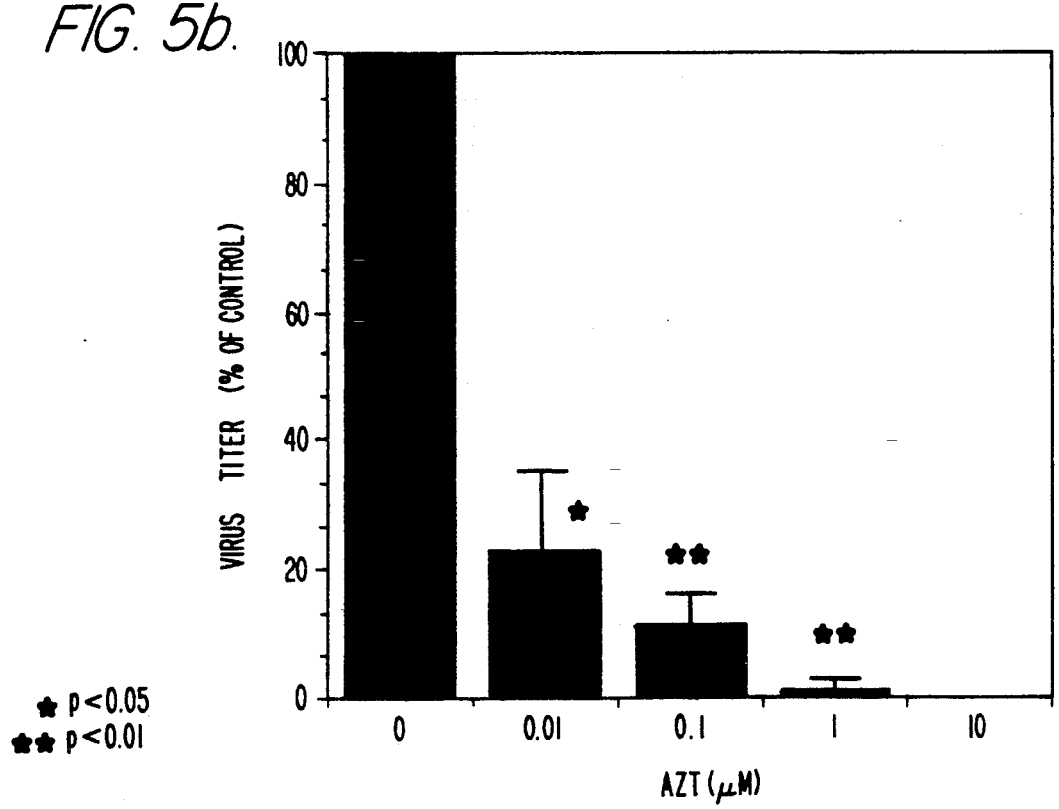
FIG. 5(b). Reduction in the virus titer as a percent of control following 24 hour preincubation of the HIV infected human T cell line SupT-1 with AZT. The p values compare treated with untreated cells.

The virus titer results of three assays carried out as in Example Three were averaged and plotted as a percentage of control and are shown in FIG. 4. AZT was 100% effective against the AIDS virus at or above 10 $\mu$M in the Example Four SupT-1 syncitial assay, as shown in FIG. 5b. The use of AZT at lower concentrations (0.01 $\mu$M-1 $\mu$M), as well as AICA riboside at concentrations of 5 $\mu$M-500 $\mu$M, were less than 100% effective, but had a good dose response relationship with the prevention of syncitial formation, as shown in FIGS. 5a and 5b.

Figure 6A:
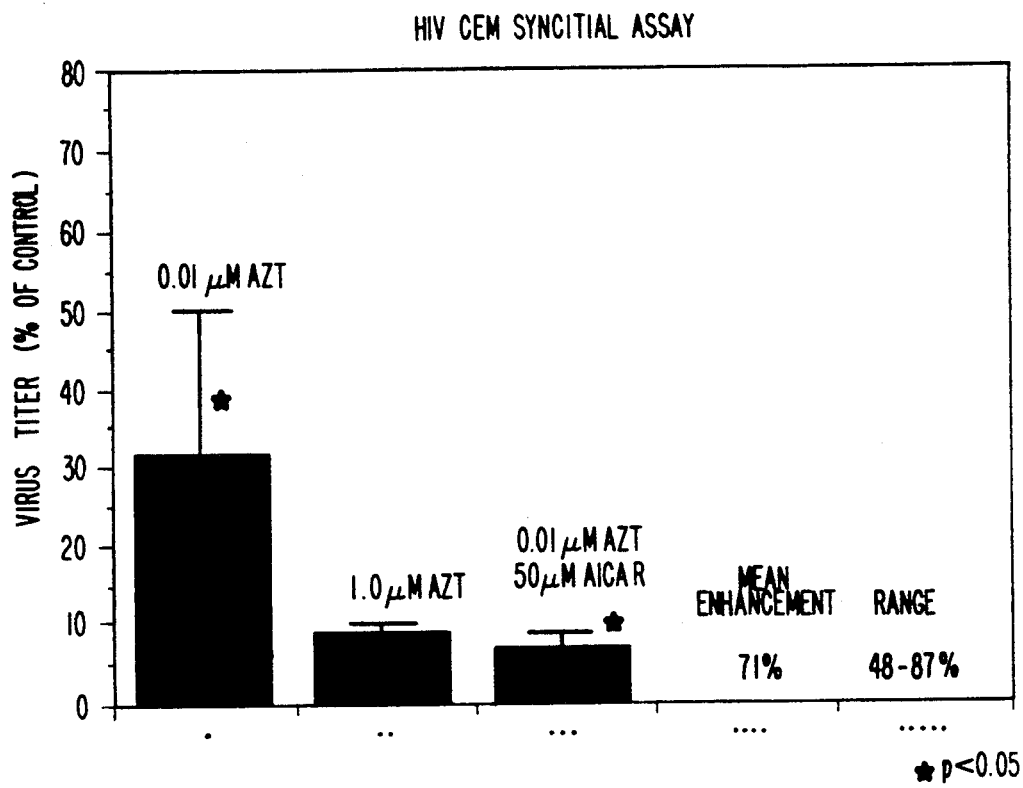
FIG. 6(a). Reduction in the virus titer as a percent of control averaged from three experiments using AZT in combination with AICA riboside in the HIV infected human T-cell line[s (a)] CEM [and (b) SupT-1].
Figure 6B:
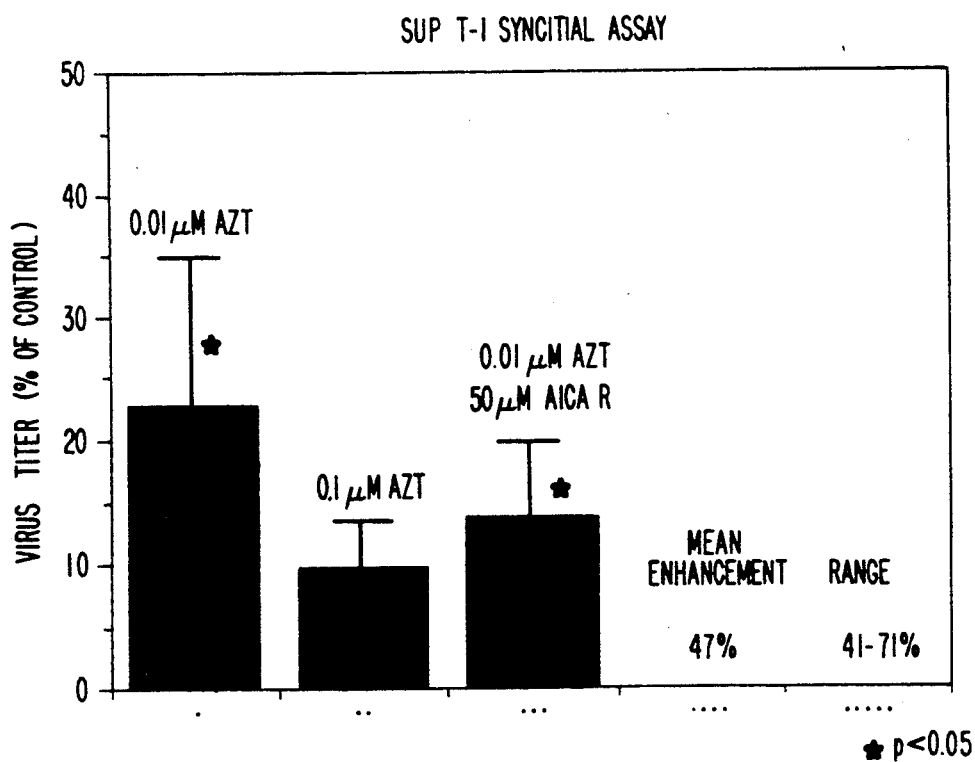
FIG. 6(b). Reduction in the virus titer as a percent of control averaged from three experiments using AZT in combination with AICA riboside in the HIV infected human cell line SupT-1.
Figure 10A:
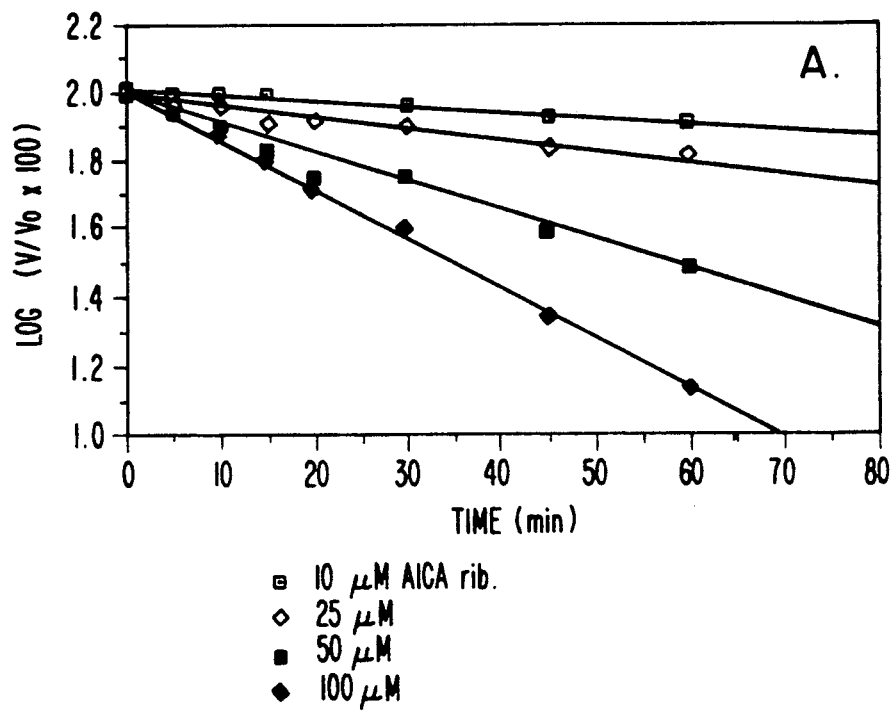
FIG. 10(a). Effect of incubation time and AICA riboside concentration on SAH hydrolase activity.
Figure 10B:
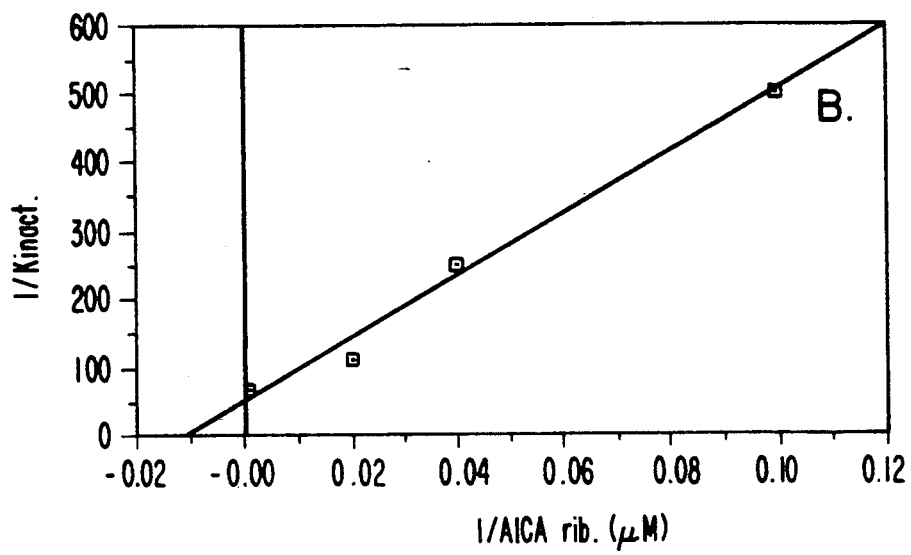
FIG. 10(i b). A plot of the reciprocal of $K_{inactivation}$ versus the reciprocal of AICA riboside concentration.

Significantly, other assays performed as described in Examples Three and Four demonstrated that the use of 50 $\mu$M AICA riboside in combination with AZT at 0.01 $\mu$M on HIV in two different human T-cell lines gave the same level of antiviral effect as from 10–100 times this amount of AZT alone. In the CEM syncitial assay, a dose of 1.0 $\mu$M AZT was as effective as 0.01 $\mu$M AZT when the latter was administered in combination with 50 $\mu$M AICA riboside (FIG. 6a). In this Example, the dose of AZT may thus be reduced 100-fold for the same effect when using AZT without AICA riboside. Similarly, in the SupT-1 assay, 0.1 $\mu$M AZT was as effective as 0.01 $\mu$M AZT coadministered with 50$\mu$M AZT (FIG. 6b). FIG. 10, which plots the results of Example Five, shows the inhibition of SAH hydrolase by AICA riboside.

AICA riboside may be chemically modified to yield an AICA riboside prodrug wherein one or more of the (2'-, 3'- or 5'-) hydroxyl oxygens of the ribosyl moiety is substituted with a hydrocarbyloxycarbonyl or hydrocarbylcarbonyl moiety. These compounds function as prodrugs of AICA riboside and are better absorbed from the gastrointestinal system. It is believed that the modifying ester side groups allow for improved capabilities in absorption from the gastrointestinal system and in reduced first pass metabolism, as well as in making more drug available for crossing the blood-brain barrier. As the prodrug molecule approaches or reaches the active site, intact modifying groups can be endogenously cleaved to regenerate AICA riboside. Described is a series of prodrugs of AICA riboside having advantageous theraputic properties, useful as antivirals and to enhance the activity of AZT. The structures of these prodrug compounds are depicted in Table I and the preparation of representative compounds is set forth. Similar modifications are made by the methods described to generate prodrugs of carbocyclic AICA riboside. Carbocyclic AICA riboside can be produced by the method described in Arita et al., *Nucleic Acids Research Symposium Series,* Vol. 12, p. 25–28 (1983), which reports the making of this compound for use as an intermediate.

Figure 7:
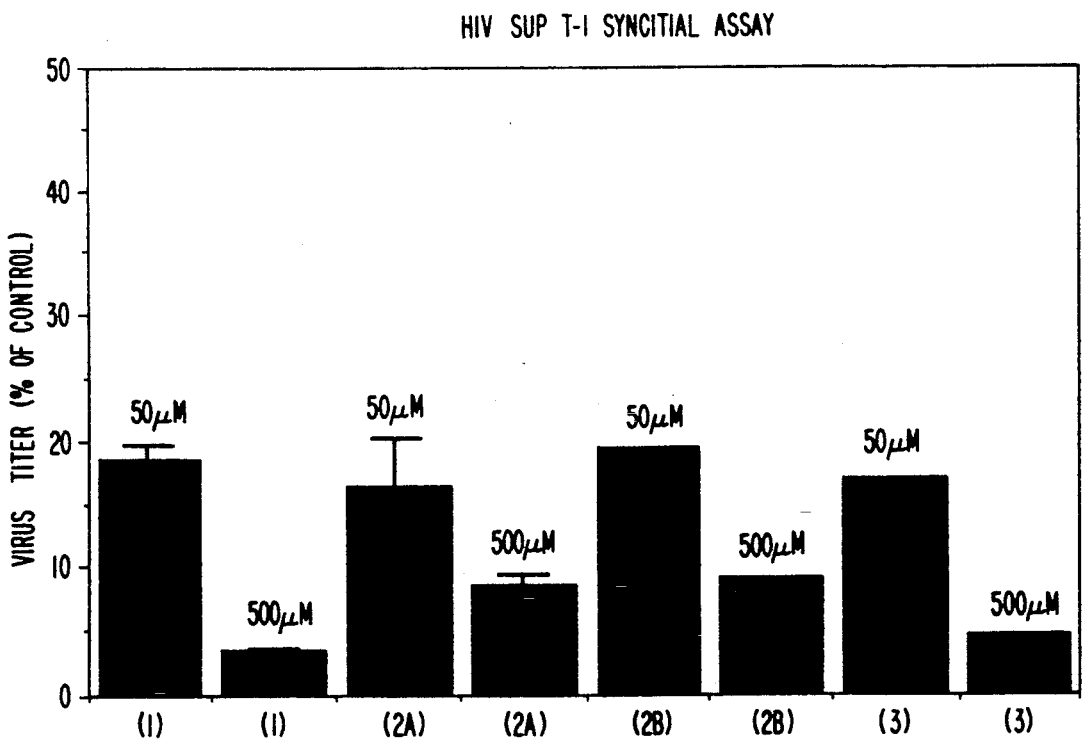
FIG. 7. Reduction in the virus titer as a percent of control using (1) AICA riboside, (2) 5-amino-3'-(2- methyl-1-propoxycarbonyl)-1-β-D-ribofuranosyl-imidazole-4-carboxamide (or "3'-isobutoxycarbonyl AICA riboside") (preparations A and B), and (3) 5-amino-3'-(1-propoxycarbonyl)-1-β-D-ribofuranosyl-imidazole-4-carboxamide in HIV infected SupT-1 cells.

The results of Example Four using various AICA riboside prodrugs as antivirals are plotted in FIG. 7. These experiments showed that the prodrugs were as effective as AICA riboside at concentrations of 50 μM. Each prodrug had significant antiviral activity in this SupT-1 syncitial assay for antiviral activity against HIV.

Preferred prodrug compounds used according to the present invention include those having the following formula:

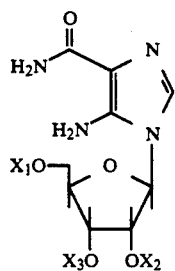
(I)

wherein $X_1$, $X_2$, and $X_3$ are independently hydrogen or

wherein $R_1$ and $R_2$ are independently hydrocarbyl preferably of from 1 to about 24 carbon atoms, or two of $X_1$, $X_2$ and $X_3$ taken together form a cyclic carbonate group, with the proviso that not all of $X_1$, $X_2$ and $X_3$ are hydrogen. Preferred $R_1$ and $R_2$ groups include lower alkyl groups, and especially preferred are those having at least one secondary carbon atom. Hydrocarbyl groups having more than 24 carbon atoms may be used and are considered to be within the scope of the present invention.

Preferred compounds include those having one or two ester groups. More preferred are those having one ester group. Especially preferred are compounds having an ester group at either the 3'- or 5'- position of the ribosyl ring.

One preferred class of compounds is the carbonate esters.

Particularly preferred are compounds wherein $X_1$ or $X_3$ is

In one especially preferred compound, $X_1$ and $X_2$ are hydrogen and $X_3$ is isobutoxycarbonyl.

The preferred carbonate ester and acyl ester compounds of the present invention may be conveniently prepared according to the following reaction scheme:

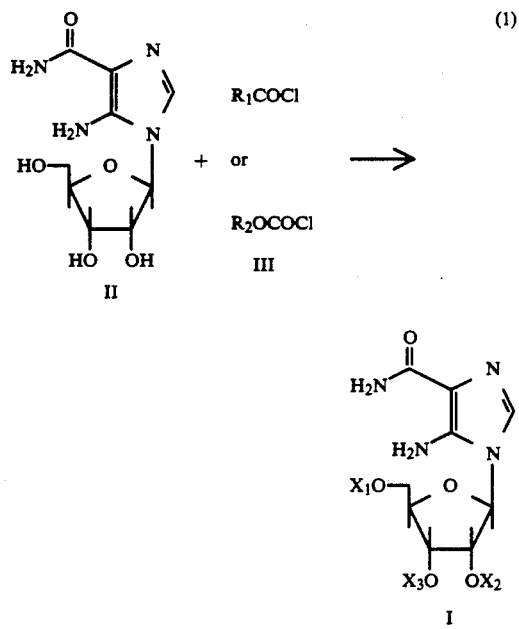

wherein $X_1$, $X_2$, $X_3$, $R_1$, and $R_2$, are as defined in conjunction with formula (I).

Reaction (1) is carried out by combining II, AICA riboside, and III, the appropriate acid chloride or chloroformate, in solvents. The acid chloride may be conveniently prepared by conventional procedures such as reaction of the corresponding acid with thionyl chloride; some acid chlorides are commercially available. Many chloroformates are commercially available; also, the chloroformates may be conveniently prepared by conventional procedures known to those skilled in the art by the reaction of phosgene with the appropriate alcohol. Reaction (1) is conducted at a temperature of from about −10° C. to about 5° C., preferably from about −5° C. to about 0° C. and is generally complete within about 2 to about 4 hours. For ease of handling, the reaction is carried out in solvents. Suitable solvents include dimethylformamide (DMF), pyridine, methylene chloride and the like. For convenience, the reaction is carried out at ambient pressure. The reaction product(s) are isolated by conventional procedures such as column chromatography, crystalization and the like. As may be appreciated, the reaction may result in a mixture of products, i.e., mono, di, and tri-esters at the 2', 3' and/or 5' positions of the ribosyl moiety. The product esters may be separated by conventional procedures such as thin layer chromatography (TLC), high pressure liquid chromatography (HPLC), column chromatography, crystalization, and the like which are well known to those skilled in the art.

The 5'-monoesters may be conveniently prepared according to the following reaction scheme to give an intermediate blocked at the 2' and 3' positions.

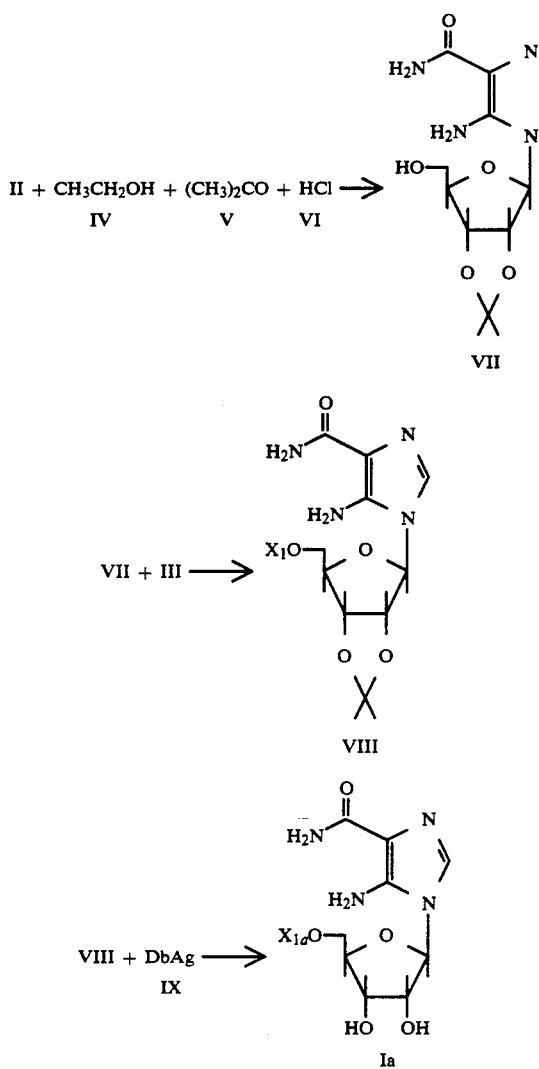

wherein $X_{1a}$ is

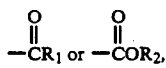

and DbAg is a deblocking agent.

Reaction (2) is conducted by combining II, IV, V and VI. Although the reactants may be combined in any order, it may be preferred to add II to a mixture of IV, V and VI. The reaction is carried out at a temperature of about 10° C. to about 25° C., preferably from about 15° C. to about 25° C. and is generally complete within about 5 hours. Intermediate VI is isolated by conventional procedures.

Reaction (3) is the reaction of intermediate VII with the appropriate acid chloride or chloroformate and is carried out as described in connection with Reaction (1).

Reaction (4) is an optional step to remove, if desired, the cyclic blocking group from the 2' and 3' positions. It is carried out by reacting with IX, the appropriate deblocking agent. Suitable deblocking agents include H+ resin in water/acetone, tetraethyl-ammonium fluoride/THF, acetic acid/water, and the like. Such deblocking reactions are conventional and well known to those skilled in the art.

Mixed ester compounds may be conveniently prepared by first reacting AICA riboside with the appropriate acid chloride according to Reaction (1) to add the acyl ester group and then reacting the acyl ester-substituted compound with the appropriate chloroformate according to Reaction (1) to obtain the mixed ester.

To assist in understanding the present invention, the results of a series of experiments follow. The following examples relating to the present invention should not, of course, be construed as specifically limiting the invention, and such equivalents of the invention now known or later developed are to be considered to fall within the scope of the present invention as hereinafter claimed.

EXAMPLE ONE

Lymphoblast Assay for the Assessment of Antiviral Candidates Effects of Cell Growth Several lymphoblast lines were utilized in conjunction with varying doses of antiviral agents to determine their effects on cell growth. In this method a daily cell count over a period of time, post-addition of antiviral compounds, can be compared with the normal cell growth curve.

Two representative T-cell lines, SupT-1 and CEM, and a B-cell line, WI-L2, were grown to mid-log phase $5 \times 10^5$ cells/ml in 50 ml of RPMI 1640 (Irvine Scientific) supplemented with 10% heat-inactivated fetal calf serum (Gemini-Bioproducts) and 1% glutamine (Gibco) to standardize seeding conditions and to assure a population of logarithmically growing cells.

An appropriate number of T-25 flasks (Corning) were seeded with evenly suspended cells at $0.5 \times 10^5$ cells/ml in 20 ml of fresh growth media. Including a control condition, each set of flasks was treated with a dose range of antiviral compound for each cell line. Each dose condition was repeated in triplicate. All flasks were incubated for 5 days at 37° C. in a 5% $CO_2$ incubator.

Every 24 hours for 5 days, three 0.2 ml samples of each flask were diluted in 9.8 ml of isoton (Fisher Scientific) and counted on a cell counter (Coulter Co.). The average of each flask was recorded, and the average of each triplicate antiviral does was then averaged and recorded.

Figure 8A:
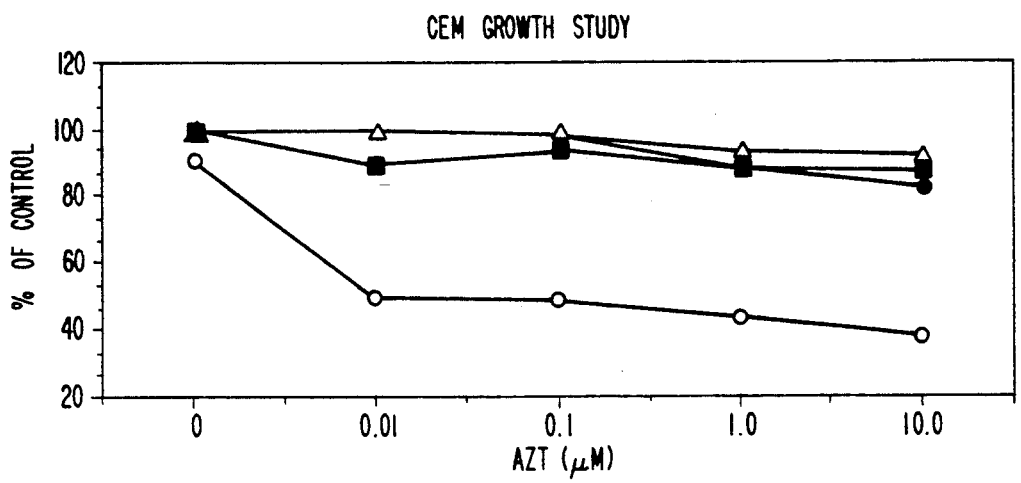
FIG. 8(a). Growth curves showing the effect of AICA riboside in the presence of AZT, on T-cell growth using the [(a)] CEM [and (b) SupT-1] cell line[s and (c) on B-cell growth using the WI-L2 cell line].
Figure 8B:
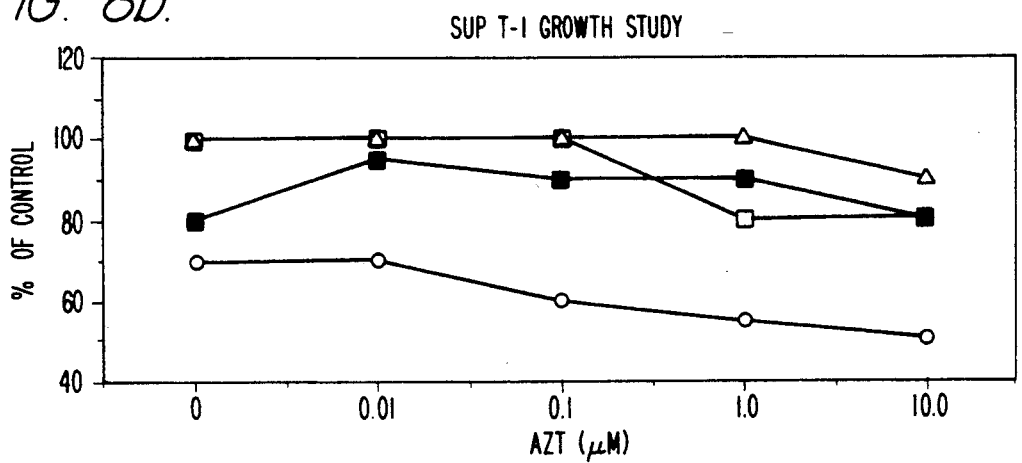
FIG. 8(b). Growth curves showing the effect of AICA riboside, in the presence of AZT, on T-cell growth using the SupT-1 cell line.
Figure 8C:
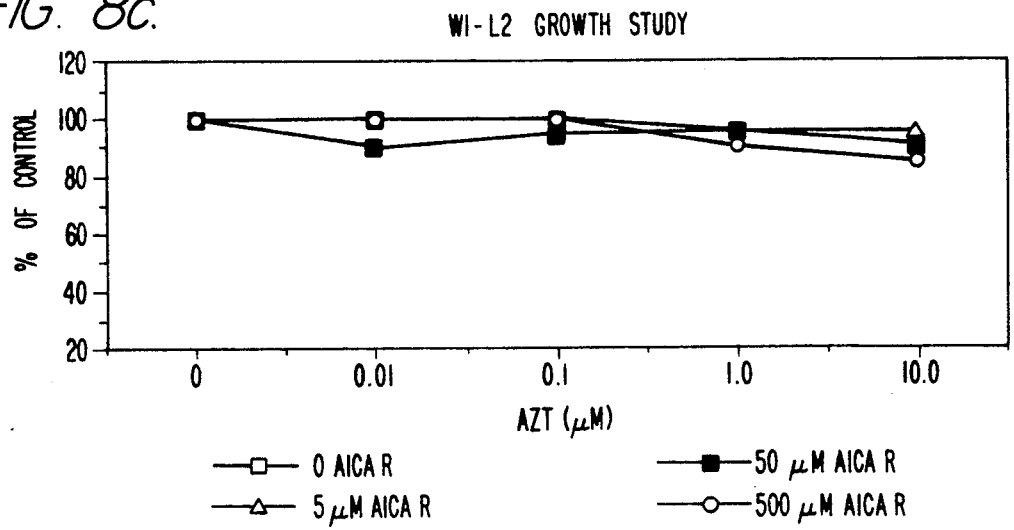
FIG. 8(c). Growth curves showing the effect of AICA riboside, in the presence of AZT, on B-cell growth using the WI-L2 cell line.
Figure 9:
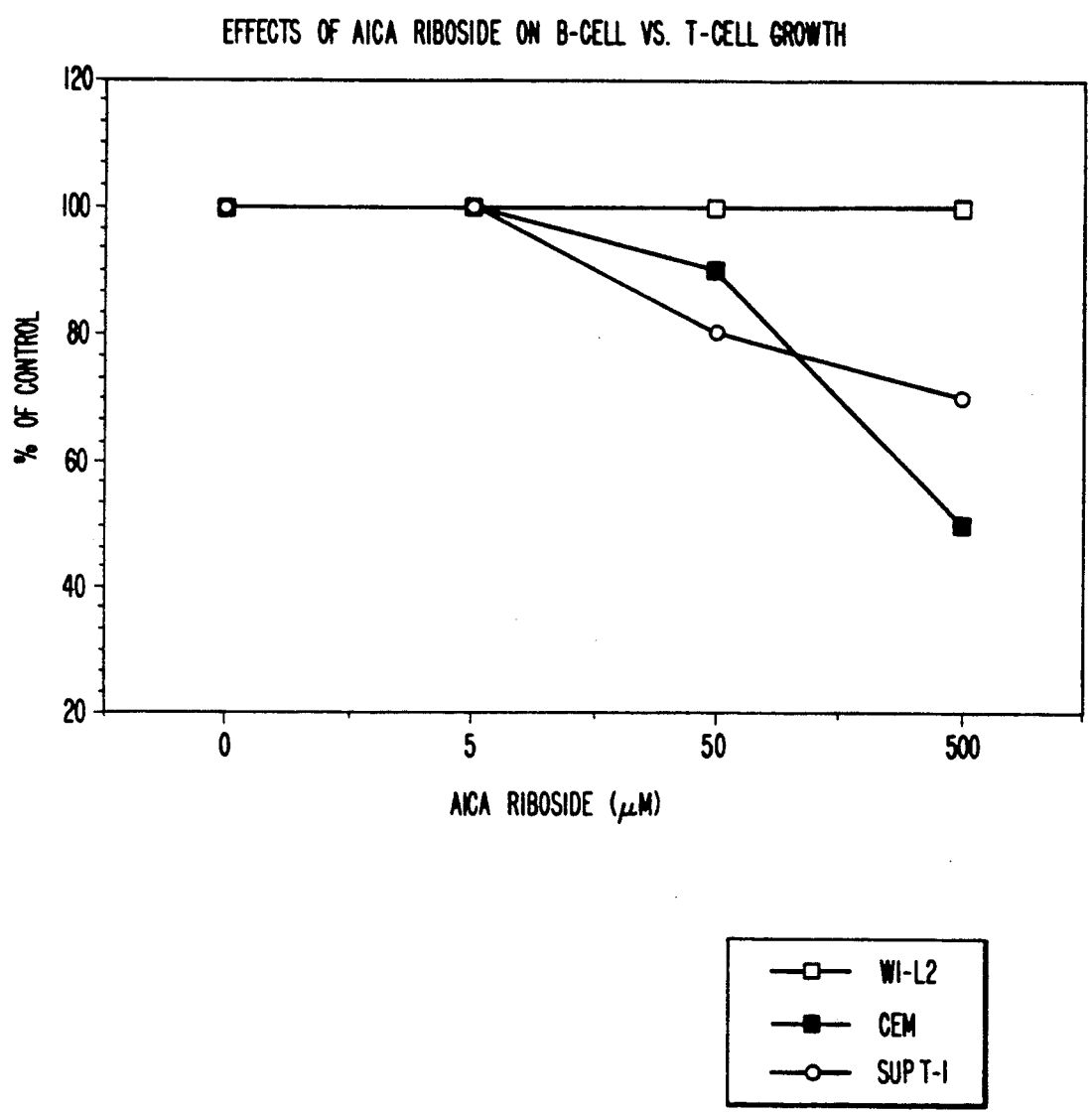
FIG. 9. Growth curves showing the effect of AICA riboside on T-cell growth and B-cell growth.

FIG. 8(a) shows that concentrations of AICA riboside from 0 to 50 μM in combination with concentrations of AZT from 0 to 10 μM had little, if any, effect on CEM cell growth. Only at 500 μM AICA riboside was there a significant decrease in cell growth. The decrease in cell growth did not vary significantly at this 500 μM AICA riboside concentration when the AZT concentration was varied from 0.01 to 10.0 μM AZT. The results in FIG. 8(b) on the Sup T-1 cell line were quite similar. FIG. 8(c) shows no significant effect on the growth of WI-L2 cells at all AICA riboside and AZT concentrations.

FIG. 9 shows the effects of AICA riboside on B-cell versus T-cell growth. AICA riboside had no effect on WI-L2 (B-cell) growth at concentrations up to 500 μM. AICA riboside showed from about 30 to about 50% reduction in T-cell growth (CEM and SUP T-1) cells at a concentration of 500 μM.

EXAMPLE TWO

Colony Resistance Assays for the Detection of Antiviral Compounds

In this colony-forming bioassay for the characterization of antiviral compounds against retroviruses, a replication-defective retroviral vector construct having the ability to confer neomycin-resistance (U937/BAG or N2) is psuedotyped, infects a single cell, and under neomycin selection, allows the recipient cell to form a colony. Since each infection yields a neomycin-resistant cell capable of producing a discrete group of cells, colonies can be counted, resulting in a linear relationship between the number of colonies and the first order of virus concentration. Through this method prospective antiviral candidates can be screened. Three separate murine retrovirus assays were utilized &:o demonstrate the antiviral effectiveness of the purine nucleosides described herein. The results are shown in FIG. 1.

U937/BAG+MA: U937 cells carrying a retroviral vector construct termed BAG (Cepko, supra) were grown to $5.0 \times 10^5$ cells per ml in RPMI 1640 (Irvine Scientific) supplemented with 10% heat-inactivated fetal bovine serum (Gemini-Bioproducts), 1% 200 mM glutamine (Gibco) and 500 µg/ml neomycin (Sigma). 10 ml of $5 \times 10^5$ cells/ml were harvested and resuspended in 2 ml of media containing murine amphotrophic virus ($10^4$ titer) and incubated in a loosely-capped centrifuge tube for 1 hour at 37° C. and 5% $CO_2$. The cells were centrifuged and resuspended in 20 ml of RPMI 1640 containing 10% heat-inactivated fetal bovine serum and 1% 200 mM glutamine and incubated overnight 12–16 hours at 37° C. and 5% $CO_2$.

1 ml of log-phase 208F rat fibroblasts were plated in alpha MEM (Irvine Scientific) with 10% heat-inactivated fetal bovine serum and 1% 200 mM glutamine at $1 \times 10^5$ cells/ml, in an appropriate number of 60 mm culture dishes (Corning) and allowed to attach in the incubator for 30 minutes. The 208F cells were pretreated prior to infection with 4 µg/ml polybrene (Sigma) overnight (12–16 hours) to ensure a uniform and kinetic viral infection. Antiviral agent(s) were added in appropriate amounts and cells were pre-incubated 24 hours prior to infection with retrovirus.

The U937/BAG+MA cells were pelleted at 1200 rpm for 5 minutes and the supernatant containing neomycin-resistant virus harvested. 2 ml were placed on &:he pre-treated 208F rat fibroblasts (the cells were roughly 50% confluent). The plates were then incubated for another 24 hours.

Neomycin selection was started on appropriate plates using 500 µg/ml neomycin in the growth media. Selection was continued, changing the media three times per week, for eight days. On the eighth day post-infection, all plates were rinsed twice with phosphate-buffered saline, and fixed with 1 ml of 95% methanol (Sigma) for 30 minutes. The methanol was removed and the plates allowed to air dry overnight.

After drying, the plates were stained with 2 ml of 1:20 Glemsa (Sigma) for 1 hour. The stain was aspirated and the plates rinsed with distilled water. All colonies containing 50 or more cells were scored.

N2: 208F rat fibroblasts were grown in alpha MEM supplemented with 10% heat-inactivated fetal calf serum and 1% mM glutamine. Log-phase cells were plated onto 60 mm plates at $1 \times 10^5$ cells in 5 ml per plate, allowed to attach, and pre-treated overnight with 4 µg/ml polybrene. 24 hours prior to infection, appropriate amounts of antiviral compound were added to each condition. On the day of infection, 50 µl of $10^5$ titer N2 virus was added to the appropriate plates and allowed to incubate for 24 hours.

Neomycin selection (500 µg/ml) was begun the next day and continued for eight days post-infection, changing the media three times per week. On the eighth day of selection, plates were rinsed with two washes of PBS, fixed with 95% methanol, and stained with 1:20 Glemsa cell stain. All colonies with 50 or more aggregate cells were counted. The results using AICA riboside and AZT as antivirals are shown in FIGS. 1a–1b.

EXAMPLE THREE

HIV Syncitial Forming Assay for Antiviral Activity Using CEM-SS Cells

The following cytomorphologic infectivity bioassay was used to characterize antiviral activity against HIV-1. In the following assay a single infectious unit of virus infects a single cell and initiates a focal expression of that infection, i.e., a syncitium. Since a single infectious unit leads to a discrete response, a linear relationship exists between the number of virally-induced cytopathic effects and the first order of virus concentration. Application of this procedure in assays for virus inactivation allows for evaluation of the candidate antiviral agent.

CEM-SS (syncitium-sensitive Leu 3a-positive CEM cell line) cells were grown in RPMI 1640 cell culture media (Irvine Scientific) supplemented with 10% heat-inactivated fetal bovine serum (Gemini Bioproducts) and 1% 200 µM glutamine (Gibco). Log-phase cells were split 1:2 with the growth medium the day prior to setting up the assay to standardize plating conditions and to assure a population of logarithmically growing cells. Ninety-six-well plates (Costar) were pretreated with 50 µl of 50 µg/ml poly-1-lysine (MW=295,000 Sigma) "PLL") and were left at room temperature for 60 minutes. Residual PLL was removed with two washes of PBS. The plates were stored in the incubator until used.

On the day of the assay, the cells were counted and enough cells were harvested to plate each well with $5.0 \times 10^4$ cells per well in a volume of 200 µl (or 20 ml of $5.0 \times 10^6$ cells/ml was appropriate for each 96-well microtitre plate).

The cells were plated out on the PLL pre-treated microtitre plates at $5.0 \times 10^4$ cells/well in a volume of 200 µl. After allowing attachment for 30 minutes at 37° C. and 5% $CO_2$, the antiviral agent(s) were added in the noted amounts and the treated plates were pre-incubated for 24 hours.

The HIV-1 virus stock (isolated from infected H-9 cells) was diluted in growth medium to yield 100 SFU (syncytial-forming units) per well. Diluted HIV-1 virus, 20 µl, was added to appropriate wells. All the plates were then incubated for 5 days at 37° C. and 5% $CO_2$. On day 5 post-infection, the cells were given a 100 µl media change. On day 7 post-infection, a syncitia count was made at 40X. The results are plotted in FIGS. 2–4 and 6(a).

EXAMPLE FOUR

HIV Syncitial Forming Assay for Antiviral Activity Using SupT-1 Cells

The assay was performed following the procedure described in Example Three except that SupT-1 cells were used. Using the SupT-1 cells, the medium was not changed at day 5 post-infection and the syncitia were counted at day 5 post-infection at 40X. The results are plotted in FIGS. 5, 6(b), and 7.

EXAMPLE FIVE

SAH Hydrolase Inhibition

The effect of incubation time and AICA riboside concentration on SAH hydrolase activity was determined as follows. Five samples of SAH hydrolase were incubated at the following AICA riboside concentrations: 0, 10, 25, 50 and 100 μM. The incubation buffer consisted of 25 mM potassium phosphate pH 7.0, 1 mM EDTA, 1 mM, DTT and 0.04% BSA. The total enzyme added to incubation mixture was 10 μg. At indicated times, 10 μl of sample was withdrawn and assayed in the following assay system: 25 mM potassium phosphate, pH 7.0, 40 mM DL-Homocysteine, 1 mM EDTA, 1 mM DTT, 10 μM EHNA, 0.1% BSA and 10 μM U-$^{14}$C Adenosine (590 m Ci/mmole). The reaction was stopped by adding 15 μl of 30% TCA. The samples were then centrifuged and 15 μl were removed and applied to Kodak cellulose 13254 TLC plates along with SAH and adenosine markers. The plates were then developed in a solvent system of 1-butanol:methanol:-H$_2$O:ammonium hydroxide (60:20:20:2). The adenosine and S-adenosyl homocysteine were visualized under UV light and the spots were cut from the plate. Radioactivity of the spots was determined by liquid scintillation spectrometry. The $K_{inactivation}$ values were determined from the slope of the log % (V/V.×100) vs. time (min.) shown in FIG. 10(a). From a plot of the reciprocal of $K_{inactivation}$ vs. 1/AICA riboside concentration the values of $K_i$ (X-intercept) and $K_{max}$ (Y-intercept), were determined (FIG. 10(b)).

EXAMPLE SIX

Preparation of Carbonate Esters of AICA Riboside

Carbonate esters of AICA riboside are prepared according to the following procedure. Carbonate esters of carbocyclic AICA riboside are similarly prepared. A 70 mmol portion of AICA riboside is suspended in a mixture of 50 ml N, N-dimethylformamide and 50 ml pyridine and then cooled in an ice-salt bath. To the resulting mixture the appropriate chloroformate (94 mmol, a 20 percent excess) is added under anhydrous conditions over a period of about 15 to 30 minutes with constant stirring. The salt bath is removed. The reaction mixture is allowed to warm to room temperature over about 1 to 2 hours. The progress of the reaction is monitored by TLC on silica gel, eluting with 6:1 methylene chloride:-methanol. Disappearance of AICA riboside indicates completion of the reaction. The solvents are removed by evaporation under high vacuum (bath temperature less than 40° C.). The residue is chromatographed on a silica gel column packed with methylene chloride and is eluted initially with methylene chloride and then with methylene chloride: methanol 95:5. Fractions showing identical (TLC) patterns are pooled and then the eluate is evaporated to give a foam. The foam is dried overnight under high vacuum at room temperature.

The yield of the product carbonate esters is about 45 to 65%. Although the primary product is the 5'-carbonate ester, other product esters are prepared.

EXAMPLE SEVEN

Preparation of 3'-Isobutoxycarbonyl AICA Riboside

A solution of AICA riboside (18.06 g, 70 mmol) in a mixture of pyridine (50 ml) and N.,N-dimethylformamide (50 ml) was cooled in an ice-salt mixture. To it was added an isobutyl chloroformate (11.47 g, 94 mmol) slowly over a period of 30 minutes with constant stirring. The initial red color of the reaction turned pale yellow in about 40 minutes. Stirring was continued for 2 hours at the end of which TLC on silica gel, eluting with methylene chloride: methanol 9:1 (Rf=0.3), indicated completion of the reaction. Methanol (2 ml) was added to neutralize unreacted reagents. The solvents from the reaction mixture were removed by evaporation under high vacuum (bath temperature approximately 40.C). The sticky mass remaining was chromatographed over a silica gel column packed in a 9:1 methylene chloride: methanol mixture. The column was eluted with the same mixture and several fractions were collected. Fractions showing identical TLC spots were pooled and evaporated to obtain an off-white foam. The product isolated from the foam had the assigned structure, based on the nmr spectrum: 3'-isobutyloxycarbonyl-AICA riboside. Yield 8.5g; mp 71°-73° (not a sharp mp) IR (nujol) 1725 cm$^{-1}$ (—OCO$_2$CH$_2$CH(CH$_3$)$_2$), nmr(DMSO-d$_6$), δ ppm, 0.9 [d, 6H (CH$_3$)$_2$], 1.9 (m, 1H, CH of isobutyl side chain), 3.6 (m, 2H, 5'-CH$_2$), 3.9 (d, 2H, CH$_2$ of isobutyl side chain), 4.1(m, 1H, 4'-CH), 4.6(1, 1H, 2'-CH), 5.01(dd, 1H, 3'-CH), 5.45-5.55(m, 2H, 1'-CH and 5'-OH), 5.92(d, 1H, 2-OH), 6.02(br.s, 2H, 5-NH$_2$), 6.6-6.9(br. d, 2H, 4-CONH$_2$), 7.35 (S, 1H, 2-CH).

The spectra of this compound was compared with that of its parent compound, AICA riboside and showed that 3'-CH (which appears at 4.05 ppm in AICA riboside), had shifted downfield by 1 ppm due to a substitution on the oxygen attached to the same carbon atom, while the positions of all the other protons remained unchanged for the most part, thus confirming the substitution to be on 3'-C.

Although nmr of the product of Example Seven indicated that it was at least 80% of the 3'-isobutoxycarbonate ester, HPLC analysis showed several peaks. The fractions corresponding to each peak were collected and analyzed on HPLC. Each peak also showed the presence of two major products, designated A and B. One of them (product A) was determined to be AICA riboside and the other (product B) was isolated in small quantities and characterized as AICA riboside-2',3'-cyclic carbonate based on its nmr and mass spectral data. nmr(DMSO-d$_6$) δ ppm, 3.6-3.7(m, 2H, 5'-CH$_2$), 4.3 (q, 1H, 4'-CH), 5.35 (m, 1H, 3'-CH), 5.6 (m, 1H, 2'-CH), 5.2-6.7 (br, 1H, 5'-OH), 5.8-6.0 (br, 2H, 5-NH$_2$), 6.1 (d, 1H, 1'-CH), 6.7-6.95(br, d, 2H, 4-CONH$_2$), 7.45 (S, 1H, 2-CH).

Mass spec, (FAB) M$^+$, 284; M$^{+1}$ 285, M$^{+2}$ 286. These data confirmed the structure of the compound (product B) to be 2',3'-cyclic carbonate of AICA riboside. A preferred method of synthesis of this compound is set forth in Example Eight below.

EXAMPLE EIGHT

Preparation of AICA 2′, 3′-Cyclic Carbonate

To a suspension of AICA-riboside (5.16 g, 20 mmol) in pyridine (50 ml), p-nitrophenyl chloroformate 92.5 g, 25 mmol) was added in one lot and stirred at room temperature for 5 days at the end of which TLC on silica gel, eluting with methylene chloride: methanol, (6:1 Rf=0.4), indicated completion of the reaction. Pyridine from the reaction mixture was removed by evaporation. The residue was chromatographed over a silica gel column, eluting with methylene chloride:methanol (9:1). The fractions which showed identical TLC were pooled and evaporated to obtain a foam (yield, 4.0 g). This product was identical to AICA riboside-2′,3′-cyclic carbonate, isolated as one of the by-products from the synthesis described in Example Seven and characterized by nmr and mass spectral analysis.

EXAMPLE NINE

Preparation of 5′-Acetyl AICA Riboside

To a mixture of dry HCe gas (9.0 g) dissolved in dry acetone (115 ml) and absolute ethanol (138 ml), AICA-riboside (12.9 g) was added. The mixture was stirred at room temperature for two hours. Completion of the reaction was monitored by TLC. The reaction mixture was stirred an additioal two hours at room temperature at which time TLC indicated that the reaction was complete. The reaction mixture was poured slowly into an ice-cold mixture of ammonium hydroxide (18 ml) and water (168 ml). The pH of the solution was adjusted to about 8 by adding a few ml of ammonium hydroxide. The reaction was concentrated to 100 ml. The ammonium chloride precipitate was removed by filtration. The filtrate was concentrated again to precipitate additional ammonium chloride. After filtering, the filtrate was evaporated to dryness. The residue was extracted three times with 200 ml aliquots of methylene chloride. Evaporation of methylene chloride gave a foam which was characterized by nmr spectroscopy to be the products 2′,3′-isopropylidene AICA riboside which was used in the following reaction without further purification.

To a solution of 2′,3′-isopropylidene AICA riboside in 25 ml. dry pyridine cooled in an ice-salt mixture, 10 ml acetic anhyydride was added dropwise with stirring; the mixture was warmed to room temperature over a period of two hours. The reaction was shown to be complete by TLC (9:1 methylene chloride: methanol). The solvents were removed from the reaction mixture by evaporation. The residue was coevaporated twice with two 25 ml aliquots of N, N-dimethylformamide. That product was treated with 100 ml of 80% acetic acid for twenty-four hours. Completion of the reaction was indicated by TLC on silica gel eluting with 6:1 methylene chloride:methanol. Water and acetic acid were removed by evaporation under reduced pressure. The residue was coevaporated four times with 100 ml aliquots of water to remove the acetic acid. The residue was crystallized from 25 ml 1:1 ethanol:water. The crystalline product was collected by filtration, washed with water and dried under vacuum to give 3.0 g of the above-identified product, melting point 165°–166° C. IR (nujol), 1745 cm$^{-1}$ (—OCOCH$_3$); nmr (DMSO-d$_6$), $\delta$ ppm 2.0 (S, 3H, COCH$_3$), 4.0–4.1 (m, 2H, 5′-CH$_2$), 4.1–4.4 (m, 3H,2′-CH, 3′-CH, 4′-CH), 5.3 (d, 1H, 1′-CH), 5.4–5.6 (m, 2H, 3′-OH, 4′-OH), 5.7–5.9 (br, 2H, 5-NH$_2$), 6.6–7.0 (br d, 2H, CONH$_2$), 7.3 (S, 1H, 2-CH).

By using the following procedures described in Examples Six to Nine and in the Detailed Description of the Invention the compounds listed in Table I were prepared. The compounds listed in Tables II and III are prepared by these procedures as well.

TABLE I

Compounds of the formula:

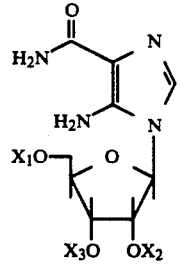

| Compound | X$_1$ | X$_2$ | X$_3$ |
|---|---|---|---|
| 1 | —H | —H | —COCH$_2$CH(CH$_3$)$_2$ (O=) |
| 2 | —COCH$_2$CH(CH$_3$)$_2$ (O=) | —COCH$_2$CH(CH$_3$)$_2$ (O=) | —H |
| 3 | —COCH$_2$CH$_3$ (O=) | —H | —H |
| 4 | —COCH$_2$CH$_2$CH$_3$ (O=) | —H | —H |
| 5 | —COCH$_2$CH$_2$CH$_3$ (O=) | —COCH$_2$CH$_2$CH$_3$ (O=) | —H |

TABLE I-continued

Compounds of the formula:

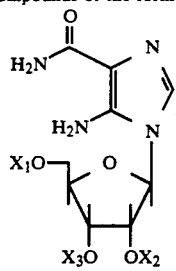

| Compound | $X_1$ | $X_2$ | $X_3$ |
|---|---|---|---|
| 6 | —CO—(CH$_2$)$_5$CH$_3$ (C=O) | —H | —H |
| 7 | —CCH$_3$ (C=O) | —H | —H |
| 8 | —H | —CCH$_3$ (C=O) | —CCH$_3$ (C=O) |
| 9 | —H | —CCH$_3$ (C=O) | —H |
| 10 | —CCH(CH$_3$)$_2$ (C=O) | —H | —H |
| 11 | —CC(CH$_3$)$_3$ (C=O) | —H | —H |
| C1 | —CCH$_3$ (C=O) | —CCH$_3$ (C=O) | —CCH$_3$ (C=O) |

TABLE II

Compounds of the formula:

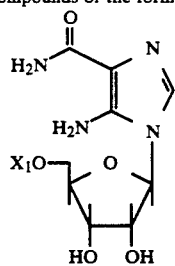

| Compound | $X_1$ |
|---|---|
| 12 | —COCH(CH$_3$)$_2$ (C=O) |
| 13 | —COC(CH$_3$)$_3$ (C=O) |
| 14 | —CO(CH$_2$)$_2$CH(CH$_3$)$_2$ (C=O) |
| 15 | —COCH$_2$—C$_6$H$_5$ (C=O) |

TABLE II-continued

Compounds of the formula:

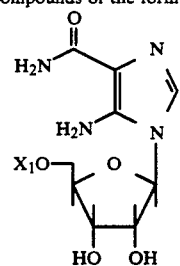

| Compound | $X_1$ |
|---|---|
| 16 | —CCH$_2$CH(CH$_3$)$_2$ (C=O) |
| 17 | —C(=O)—(3-pyridyl) |
| 18 | —C(=O)—C$_6$H$_4$—O—C(=O)—C(CH$_3$)$_3$ |
| 19 | —CCH$_2$N(CH$_3$)$_2$ (C=O) |

TABLE II-continued
Compounds of the formula:
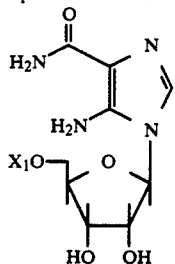
| Compound | $X_1$ |
|---|---|
| 20 | 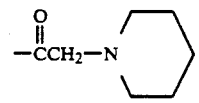 |
TABLE III
Compounds of the formula
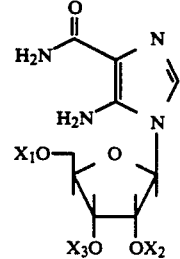
| Compound | $X_1$ | $X_2$ | $X_3$ |
|---|---|---|---|
| 21 |  | —H | —H |
| 22 | —H | —H | 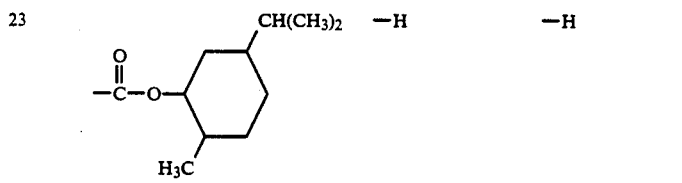 |
| 23 | 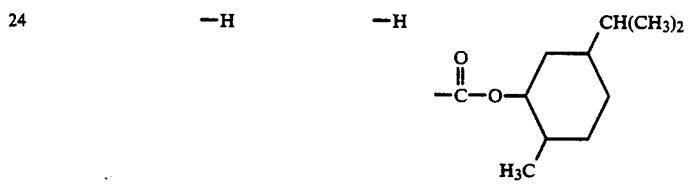 | —H | —H |
| 24 | —H | —H |  |
| 25 |  | —H | —H |
| 26 | —H | —H |  |
| 27 | —COCH$_2$CH$_2$OCH$_3$ | —H | —H |
| 28 | —H | —H |  |
| 29 | 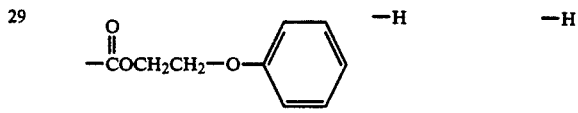 | —H | —H |

TABLE III-continued

Compounds of the formula

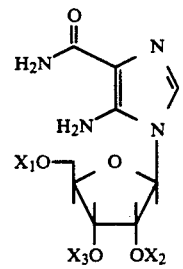

| Compound | $X_1$ | $X_2$ | $X_3$ |
|---|---|---|---|
| 30 | —H | —H | —COCH₂CH₂O—C₆H₅ (with C=O) |
| 31 | (γ-butyrolactone-C(O)O—) | —H | —H |
| 32 | —H | —H | (γ-butyrolactone-OC(O)—) |

We claim:

1. A method of enhancing the antiviral effect of AZT which comprises administering AZT in conjunction with a therapeutically effective amount of AICA riboside to a host in need of treatment.

2. A method of enhancing the antiviral effect of AZT which comprises administering AZT in conjunction with a therapeutically effective amount of an AICA riboside prodrug to a host in need of treatment.

3. The method of claim 2 wherein said AICA prodrug is selected from the group consisting of 5-amino-3'(2-methyl-1-propoxycarbonyl)-1-$\beta$-D-ribofuranosyl-imidazole-4 carboxamide and 5-amino-3'-(1-propoxycarbonyl)-1-$\beta$-D-ribofuranosyl-imidazole-4-carboxamide.

4. The method of claim 2 wherein said AICA riboside prodrug comprises a modified AICA riboside having an AICA ribosyl moiety and at least one hydrocarbyloxycarbonyl or hydrocarbylcarbonyl moiety per equivalent weight of AICA ribosyl moiety.

5. The method of claim 4 wherein at least one of the hydroxyl oxygens of the ribosyl moiety of said prodrug is substituted with a hydrocarbyloxycarbonyl or hydrocarbylcarbonyl moiety.

6. The method of claim 4 wherein at least one of the hydroxyl oxygens of the ribosyl moiety of said prodrug is substituted with a hydrocarboxycarbonyl moiety.

7. The method of claim 4 wherein said prodrug has from 1 to 2 hydrocarbyloxycarbonyl or hydrocarbylcarbonyl moieties per equivalent weight of AICA ribosyl moiety.

8. The method of claim 2 wherein said prodrug is of the formula

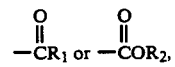

wherein $X_1$, $X_2$, and $X_3$, are independently hydrogen, $$-CR_1 \text{ or } -COR_2,$$
(with C=O)

wherein $R_1$ and $R_2$ are independently hydrocarbyl or two of $X_1$, $X_2$ and $X_3$ taken together form a cyclic carbonate group; with the proviso that not all of $X_1$, $X_2$ and $X_3$ are hydrogen.

9. The method of claim 8 wherein $R_1$ and $R_2$ of said prodrug are hydrocarbyl groups having a secondary carbon atom.

10. The method of claim 8 wherein $X_1$ or $X_3$ of said prodrug is

11. The method of claim 10 wherein $R_2$ of said prodrug has a secondary carbon atom.

12. A method of enhancing the antiviral effect of AZT which comprises administering AZT in conjunction with a therapeutically effective amount of a means for inhibiting SAH hydrolase to a host in need of treatment.

13. A method according to claim 12 wherein said means for inhibiting SAH hydrolase is a purine nucleoside.

14. A method according to claim 13 wherein said purine nucleoside is AICA riboside.

15. A method according to claim 13 wherein said purine nucleoside is an AICA riboside prodrug.

16. A method according to claim 14 wherein AICA riboside is administered in an amount from about 1 mg/kg/day to about 1000 mg/kg/day.

17. A method according to claim 14 wherein said AICA riboside prodrug is administered in an amount from about 1 mg/kg/day to about 1000 mg/kg/day.

18. The method of claim 13 wherein said means for inhibiting SAH hydrolase is carbocyclic AICA riboside.

19. The method of claim 13 wherein said means for inhibiting SAH hydrolase is a carbocyclic AICA riboside prodrug.

20. A method of increasing the antiviral activity of AZT which comprises administering AZT in conjunction with a therapeutically effective amount of a purine nucleoside or purine nucleoside analog which increase the incorporation of AZT triphosphate into DNA by reverse transcriptase to a host in need of treatment.

21. A method according to claim 20 wherein said purine nucleoside is AICA riboside.

22. A method according to claim 20 wherein said purine nucleoside increases AZT triphosphate incorporation by reducing thymidine triphosphate incorporation in DNA.

23. A method according to claim 20 wherein said purine nucleoside analog is carbocyclic AICA riboside.

24. A method according to claim 22 wherein said purine nucleoside reduces incorporation of thymidine triphosphate by reducing the intracellular thymidine triphosphate.

25. A method according to claim 24 wherein said purine nucleoside is AICA riboside.

26. A method according to claim 22 wherein said purine nucleoside reduces incorporation of thymidine triphosphate by increasing thymidine kinase activity.

27. A method according to claim 26 wherein said purine nucleoside is AICA riboside.

28. A method for decreasing or preventing viral infectivity comprising the administration of a therapeutically effective amount of AICA riboside to a host in need of treatment.

29. The method of claim 28 wherein said viral infectivity is caused by a retrovirus.

30. The method of claim 29 wherein said retrovirus is a human retrovirus.

31. The method of claim 30 wherein said human retrovirus is human immunodeficiency virus.

32. The method of claim 31 wherein AICA riboside is administered in amounts ranging from 1 mg/kg/day to about 1000 mg/kg/day.

33. The method of claim 30 wherein AICA riboside is administered in amounts ranging from 1 mg/kg/day to about 1000 mg/kg/day.

34. The method of claim 29 wherein AICA riboside is administered in amounts ranging from 1 mg/kg/day to about 1000 mg/kg/day.

35. The method of claim 28 wherein AICA riboside is administered in amounts ranging from 1 mg/kg/day to about 1000 mg/kg/day.

36. A method of decreasing or preventing viral infectivity comprising the administration of a therapeutically effective amount of an AICA riboside prodrug to a host in need of treatment.

37. The method of claim 36 wherein said viral infectivity is caused by a retrovirus.

38. The method of claim 37 wherein said retrovirus is a human retrovirus.

39. The method of claim 38 wherein said human retrovirus is human immunodeficiency virus.

40. The method of claim 39 wherein said AICA riboside prodrug is administered in amounts ranging from about 1 mg/kg/day to about 1000 mg/kg/day.

41. The method of claim 38 wherein said AICA riboside prodrug is administered in amounts ranging from about 1 mg/kg/day to about 1000 mg/kg/day.

42. The method of claim 37 wherein said AICA riboside prodrug is administered in amounts ranging from about 1 mg/kg/day to about 1000 mg/kg/day.

43. The method of claim 36 wherein said AICA riboside prodrug is administered in amounts ranging from about 1 mg/kg/day to about 1000 mg/kg/day.

44. The method of claim 36 wherein said AICA riboside prodrug is selected from the group consisting of 5-amino-3'-(2-methyl-1-propoxycarbonyl)-1-$\beta$-D-ribofuranosyl-imidazole-4-carboxamide, 5-amino-3'-1-propoxycarbonyl)-1-$\beta$-D-ribofuranosyl-imidazole-4-carboxamide, and 2'3'-cyclocarbonate AICA riboside.

45. A method of enhancing the antiviral effect of AZT which comprises administering AZT in conjunction with a therapeutically effective amount of AICA to a host in need of treatment.

46. A method of enhancing the antiviral effect of AZT which comprises administering AZT in conjunction with a therapeutically effective amount of an AICA riboside analog to a host in need of treatment.

47. The method of claim 46 wherein said AICA riboside analog is 5-amino-3'-(2-methyl-1-propoxycarbonyl)-1-$\beta$-D-ribofuranosyl-imidazole-4-carboxamide.

48. The method of claim 46 wherein said AICA riboside analog is carbocyclic AICA riboside.

49. The method of claim 46 wherein said AICA riboside analog is a carbocyclic AICA riboside prodrug.

50. The method of any of claims 1, 2, 8, 14, 15, 16, 17, 21, 23, 28, 36, 44, 47, 25, 27, 35, 34, 33, 32, 43, 42, 41, and 40 further comprising the administration of a means for preventing uric acid synthesis.

* * * * *

UNITED STATES PATENT AND TRADEMARK OFFICE
CERTIFICATE OF CORRECTION

PATENT NO. : 5,132,291
DATED : July 21, 1992
INVENTOR(S) : Harry E. Gruber

It is certified that error appears in the above-indentified patent and that said Letters Patent is hereby corrected as shown below:

```
Column 5, line 32, "[and AZT]" should read --[and (b) AZT]--.
Column 15, line 17, "&:o" should read --to--
Column 15, line 48, "&:he" should read --the--
```

Signed and Sealed this

Twenty-ninth Day of August, 1995

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO. : 5,132,291
DATED : July 21, 1992
INVENTOR(S) : Harry E. Gruber

It is certified that error appears in the above-identified patent and that said Letters Patent is hereby corrected as shown below:

Column 5, Line 32: delete "[(a)]" and "[and AZT]"

Column 5, Line 43: delete "[(a)]"

Column 5, Line 44: delete "[and (b) AZT]"

Column 5, Line 52: delete "[(a)]"

Column 5, Line 53: delete "[and (b) AZT]"

Column 5, Line 62: delete "[s (a)]" and "[and (b) SupT-1]"

Column 6, Line 8: delete "[(a)]" and "[and (b) SupT-1]"

Column 6, Line 8 to 9: delete "[s and (c) on B-cell growth using the WI-L2 cell line]"

Column 15, Line 17: after utilized delete "&:o" and insert --to--

UNITED STATES PATENT AND TRADEMARK OFFICE
CERTIFICATE OF CORRECTION

PATENT NO. : 5,132,291

DATED : July 21, 1997

INVENTOR(S) : Harry E. Gruber

It is certified that error appears in the above-identified patent and that said Letters Patent is hereby corrected as shown below:

Column 15, Line 48: delete "&:he" and insert --the--

This certificate supersedes Certificate of Correction issued August 29, 1995.

Signed and Sealed this

Second Day of December, 1997

Attest:

BRUCE LEHMAN

Attesting Officer

Commissioner of Patents and Trademarks